(12) United States Patent
Hussain et al.

(10) Patent No.: US 6,185,453 B1
(45) Date of Patent: Feb. 6, 2001

(54) IONTOPHORETIC DELIVERY OF INTEGRIN INHIBITORS

(75) Inventors: Munir A. Hussain, Wilmington; Arnold J. Repta, Greenville, both of DE (US)

(73) Assignee: DuPont Pharmaceuticals Company, Wilmington, DE (US)

(*) Notice: Under 35 U.S.C. 154(b), the term of this patent shall be extended for 0 days.

(21) Appl. No.: 08/877,829

(22) Filed: Jun. 18, 1997

Related U.S. Application Data

(60) Provisional application No. 60/020,277, filed on Jun. 19, 1996.

(51) Int. Cl.⁷ .............................. A61N 1/30; A61M 1/00
(52) U.S. Cl. .............................. 604/21; 604/28; 424/449; 514/374; 514/378
(58) Field of Search ....................................... 514/374, 378; 424/449; 604/21, 28

(56) References Cited

U.S. PATENT DOCUMENTS

| | | | |
|---|---|---|---|
| 5,334,596 | 8/1994 | Hartman et al. | 514/301 |
| 5,607,691 * | 3/1997 | Hale et al. | 424/449 |
| 5,738,647 * | 4/1998 | Bernhard et al. | 604/20 |

FOREIGN PATENT DOCUMENTS

| | | |
|---|---|---|
| 0748636 | 12/1996 | (EP) . |
| 9514683 | 6/1995 | (WO) . |
| 9637492 | 11/1996 | (WO) . |

\* cited by examiner

*Primary Examiner*—Kevin E. Weddington

(57) ABSTRACT

This invention relates to novel methods and devices for iontophoretically administering therapeutic doses of integrin receptor antagonists in a controlled manner through the skin. Such integrin receptor antagonists include but are not limited to antagonists of the IIb/IIIa and $\alpha_v\beta_3$ integrins and related cell surface adhesive protein receptors. The present invention includes iontophoretic delivery devices comprising integrin inhibitors. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

11 Claims, 5 Drawing Sheets

IONTOPHORETIC DELIVERY OF INTEGRIN INHIBITORS

CROSS REFERENCE TO EARLIER FILED APPLICATION

This application claims benefit under 35 USC §119(e) of U.S. Provisional Application 60/020,277, filed June 19, 1996. The disclosure of this earlier filed application is hereby incorporated herein by reference.

FIELD OF THE INVENTION

This invention relates to novel methods and devices for iontophoretically administering therapeutic doses of integrin receptor antagonists in a controlled manner through the skin. Such integrin receptor antagonists include but are not limited to antagonists of the IIb/IIa and $\alpha_v\beta_3$ integrins and related cell surface adhesive protein receptors. The present invention includes iontophoretic delivery devices comprising integrin inhibitors. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

BACKGROUND OF THE INVENTION

A number of cell surface receptor proteins, referred to as integrins, have been identified which bind to extracellular matrix ligands or other cell adhesion protein ligands thereby mediating cell-cell and cell-matrix adhesion processes. The integrins are encoded by genes belonging to a gene superfamily and are composed of heterodimeric transmembrane glycoproteins containing $\alpha$- and $\beta$-subunits. Integrin subfamilies contain a common $\beta$-subunit combined with different $\alpha$-subunits to form adhesion protein receptors with different specificities. The genes for at least eight distinct $\beta$-subunits have been cloned and sequenced to date.

The integrin glycoprotein IIb/IIIa (GPIIb/IIIa or IIb/IIIa), also referred to as the fibrinogen receptor, is the membrane protein mediating platelet aggregation. IIb/IIIa in activated platelets is known to bind four soluble RGD-containing adhesive proteins, namely fibrinogen, von Willebrand factor, fibronectin, and vitronectin. "RGD" refers to the amino acid sequence Arg-Gly-Asp. The binding of fibrinogen and von Willebrand factor to IIb/IIIa causes platelets to aggregate. The binding of fibrinogen is mediated in part by the Arg-Gly-Asp (RGD) recognition sequence which is common to the adhesive proteins that bind IIb/IIIa. RGD-peptidomimetic IIb/IIIa antagonist compounds are known to block fibrinogen binding and prevent platelet aggregation and the formation of platelet thrombi. IIb/IIIa antagonists represent an important new approach for antiplatelet therapy for the treatment of thromboembolic disorders.

In addition to IIb/IIIa, a number of other integrin cell surface receptors have been identified. For example, members of the $\beta 1$ subfamily, $\alpha 4\beta 1$ and $\alpha 5\beta 1$, have been implicated in various inflammatory processes, including rheumatoid arthritis. In addition, studies with monoclonal anti-$\alpha 4$ antibodies provide evidence that $\alpha 4/\beta 1$ may additionally have a role in allergy, asthma, and autoimmune disorders. Anti-$\alpha 4$ antibodies block the migration of leukocytes to the site of inflammation.

The $\alpha_v\beta_3$ integrin, also referred to as the vitronectin receptor, is a heterodimer and is a member of the $\beta_3$ integrin subfamily. The $\alpha_v\beta_3$ integrin is found on platelets, endothelial cells, melanoma cells, smooth muscle cells, and osteoclasts. Like the integrin IIb/IIIa, the $\alpha_v\beta_3$ integrin binds a variety of RGD-containing adhesive proteins such as vitronectin, fibronectin, von Willebrand factor, fibrinogen, osteopontin, bone sialo protein II and thrombosponden in a manner mediated by the RGD sequence. Thus, $\alpha_v\beta_3$ acts as the endothelial cell, fibroblast, and smooth muscle cell receptor for adhesive proteins including von Willebrand factor, fibrinogen (fibrin), vitronectin, thrombospondin, and osteopontin.

The integrin $\alpha_v\beta_3$ allows endothelial cells to interact with a wide variety of extracellular matrix components. These adhesive interactions are considered to be important for angiogenesis since vascular cells must ultimately be capable of invading virtually all tissues. Integrin $\alpha_v\beta_3$ is involved in bone resorption since a key event in bone resorption is the adhesion of osteoclasts to the matrix of bone. During endothelium injury, the basement membrane zones of blood vessels express several adhesive proteins, including von Willebrand factor, fibronectin, and fibrin. Additionally, several members of the integrin family of adhesion protein receptors are expressed on the surface of endothelial, smooth muscle and on other circulating cells. Among these integrins is $\alpha_v\beta_3$. These integrins initiate a calcium-dependent signaling pathway that can lead to endothelial cell, smooth muscle cell migration and, therefore, may play a fundamental role in vascular cell biology.

Inhibitors of $\alpha_v\beta_3$ integrin have been shown to inhibit angiogenesis and are recognized as being useful as therapeutic agents for the treatment of human diseases such as cancer, restenosis, thromoembolic disorders, rheumatoid arthritis and ocular vasculopathies.

The use of iontophoresis, also referred to as electrotransport, in drug delivery is well known. The iontophoresis process has been found to be useful in the transdermal administration of therapeutic drugs including lidocaine hydrochloride, hydrocortisone, fluoride, penicillin, dexamethasone sodium phosphate, insulin and other drugs. A common use of iontophoresis is in the diagnosis of cystic fibrosis by delivering pilocarpine salts iontophoretically, where the pilocarpine stimulates sweat production and the sweat is collected and analyzed for its chloride content to detect the presence of the disease.

SUMMARY OF THE INVENTION

The present invention provides novel methods and devices for iontophoretically administering therapeutic doses of integrin receptor antagonists in a controlled manner through the skin. Such integrin receptor antagonists include but are not limited to antagonists of the IIb/IIIa and $\alpha_v\beta_3$ integrins and related cell surface adhesive protein receptors. The present invention includes iontophoretic delivery devices comprising integrin inhibitors. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

BRIEF DESCRIPTION OF THE DRAWINGS

Preferred embodiments of the invention have been chosen for purposes of illustration and description, but are not intended in any way to restrict the scope of the invention.

The preferred embodiments of certain aspects of the invention are shown in the accompanying drawings described below.

DETAILED DESCRIPTION OF THE INVENTION

Figure 1:
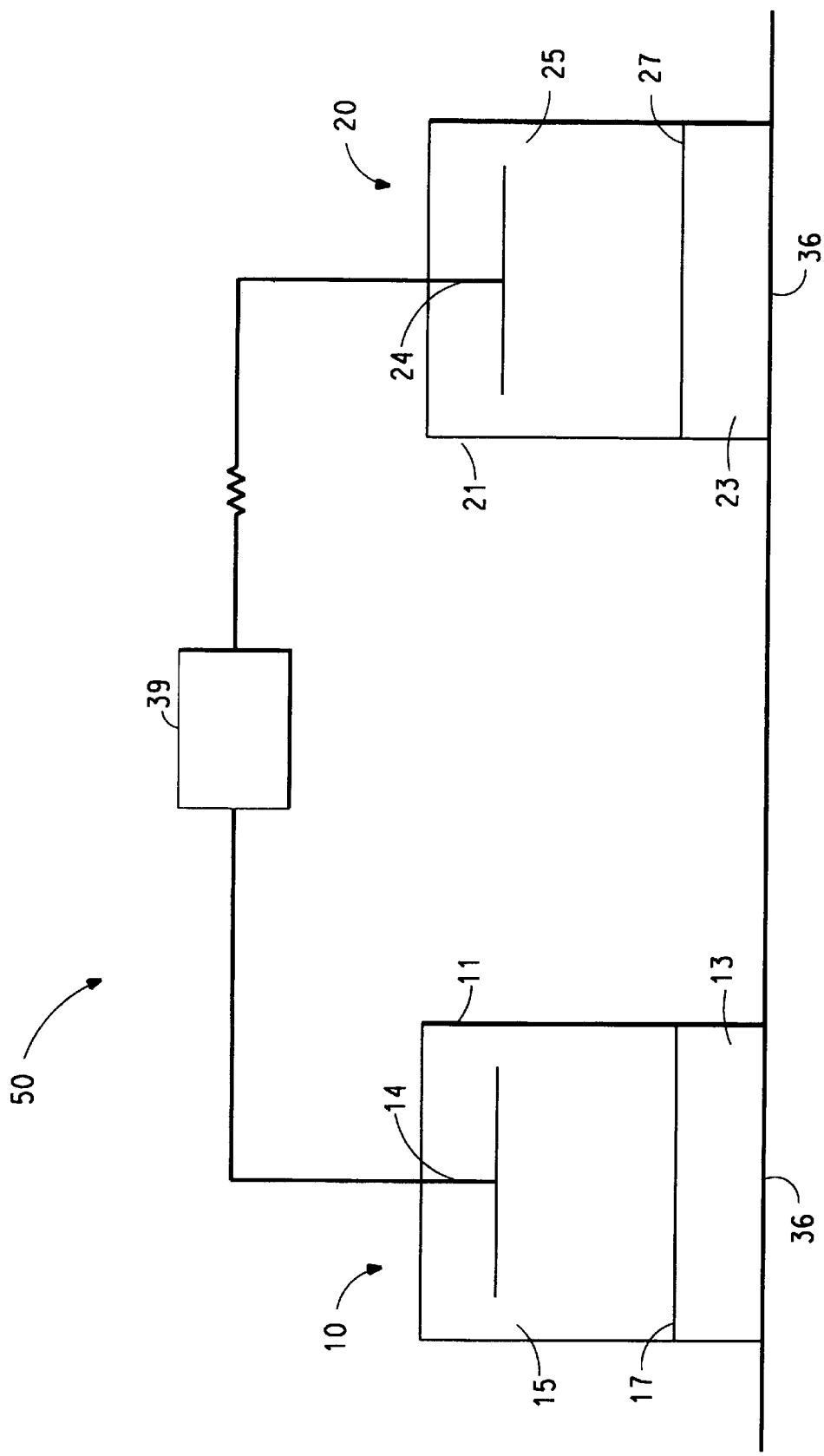
FIG. 1 depicts a cross-sectional view of a schematic iontophoretic device suitable for use according to the present invention.

The present invention provides novel methods and devices for iontophoretically administering therapeutic doses of integrin receptor antagonists in a controlled manner through the skin. Such integrin receptor antagonists include but are not limited to antagonists of the IIb/IIIa and $\alpha_v\beta_3$ integrins and related cell surface adhesive protein receptors. The present invention includes iontophoretic delivery devices comprising integrin inhibitors. Such methods and devices are useful, alone or in combination with other therapeutic agents, for the treatment of thromboembolic disorders, angiogenic disorders, inflammation, bone degradation, cancer metastasis, diabetic retinopathy, restenosis, macular degeneration, and other conditions mediated by cell adhesion and/or cell migration and/or angiogenesis.

The present invention provides novel methods of delivery of therapeutic compounds which bind to integrin proteins thereby altering cell-matrix and cell-cell adhesion processes. Such compounds, referred to herein as "integrin inhibitors" or "integrin antagonists", act as inhibitors of the binding of the integrin protein to endogenous protein ligands of such integrin. Preferred integrin inhibitors used in the present invention are RGD-peptidomimetic compounds. As used herein, the term "RGD-peptidomimetic compounds" refers to chemical compounds which bind to the RGD-binding region of the integrin and which block RGD-mediated binding of one or more adhesive proteins to such integrin.

The present invention provides a means for the controlled and continuous delivery of integrin antagonists through skin using an iontophoretic transdermal delivery device. The present invention further provides a means for attaining consistent plasma concentrations of integrin antagonists and for controlling their pharmacologic and toxic effects. The method of the present invention for delivering integrin receptor antagonists transdermally utilizes an iontophoretic transdermal drug delivery device or apparatus.

As used herein, the term "iontophoretic device" or "iontophoretic patch" or "patch" refers to a device or apparatus suitable for the transdermal iontophoretic delivery of therapeutic levels of a compound to a subject. Such iontophoretic devices are well known in the art and are also referred to as "iontophoresis devices" or "electrotransport devices".

The present invention provides methods of integrin inhibitor drug delivery which provides controlled, continuous delivery of the drug at a relatively low rate. Such controlled, continuous delivery of the integrin inhibitor ensures relatively constant plasma concentrations and control of pharmacologic and toxic drug effects. This is particularly desirable for drugs having steep dose versus response profiles, for which there are relatively small differences between ineffective, therapeutic, and toxic plasma concentrations or doses. Transdermal iontophoretic delivery provides a means of controlled, continuous drug delivery and avoids the uncertainties of oral administration and the inconvenience and discomfort of administration by injection. In addition, iontophoresis transdermal delivery methods are used in the present invention since generally the integrin inhibitor compounds do not passively diffuse through skin at rates sufficient for delivering therapeutic doses and the skin is especially impermeable to polar and ionic drugs.

The iontophoretic drug delivery device used in the present invention comprises a power source for generation of an electrical current and two electrode compartments that when adhering to the skin of a subject will pass a generated electrical current through the skin. In the presence of the electrical current the passage through the skin of the integrin antagonist, which is contained in one of the electrode compartments, is enhanced. As is appreciated by one of skill in the art of iontophoresis drug delivery, the rate of transdermal delivery of the integrin antagonist in accordance with the present invention can be controlled by selection of the patch design, including the selection of the contents of the electrode compartments, the surface area of the patch, and by the strength of the generated electrical current.

One embodiment of the present invention provides for an iontophoretic device comprising:

(a) a current distributing member;

(b) an agent reservoir containing an ionized or ionizable substance, in electrical communication with the current distributing member and adapted to be placed in ionic communication with the epithelial surface, wherein the ionized or ionizable substance is an integrin inhibitor compound;

(c) an electrolyte reservoir containing an electrolyte, in electrical communication with an indifferent electrode and in ionic communication with an epithelial surface;

(d) an electrical power source in current delivering connection with the current distribution member and the electrolyte reservoir.

This device is capable of delivering an amount of cell adhesion molecules to a patient over a period of time which provides a therapeutic concentration of cell adhesion molecules capable of inhibiting platelet aggregation.

Another embodiment of the present invention is a method of non-invasively administrating a therapeutic concentration of cell adhesion molecules to a patient. Cell adhesion molecules are iontophoretically passed through a predetermined area of skin of the patient, wherein such therapeutic concentration of cell adhesion molecules is capable of inhibiting platelet aggregation.

Iontophoretic devices useful in the present invention are described, for example, in the following U.S. Pat. Nos., the disclosures of which are incorporated herein by reference: 3,991,755; 4,141,359; 4,250,878; 4,395,545; 4,744,787; 4,747,819; 4,927,408; 5,080,646; 5,084,006; 5,125,894; 5,135,477; 5,135,480; 5,147,296; 5,147,297; 5,158,537; 5,162,042; 5,162,043; 5,167,616; 5,169,382; 5,169,383; 5,415,628; 5,203,768; 5,207,752; 5,221,254; 5,232,438; 5,234,992; 5,240,995; 5,246,417; 5,288,389; 5,298,017;

5,310,404; 5,312,326; 5,314,502; 5,320,598; 5,322,502; 5,326,341; 5,344,394; 5,374,242; 5,380,271; 5,385,543; 5,387,189; 5,395,310; 5,403,275; 5,405,317; 5,415,628; 5,423,739; 5,443,442; 5,445,606; 5,445,609; 5,464,387; 5,466,217; 4,950,229; 5,246,418; 5,256,137; 5,284,471; 5,302,172; 5,306,235; 5,310,403; 5,320,597; 5,458,569; 5,498,235; 4,557,723; 4,713,050; 4,865,582; 4,752,285; 5,087,242; 5,236,412; 5,281,287.

In general, at least two electrodes are used in the iontophoretic device. Both of these electrodes are disposed so as to be in intimate electrical contact with some portion of the skin of the body. One electrode, called the active or donor electrode, is the electrode from which the ionic integrin inhibitor drug precursor or drug is delivered into the body by iontophoresis. The other electrode, called the counter or return or indifferent electrode, serves to close the electrical circuit through the body. In conjunction with the patient's skin contacted by the electrodes, the circuit is completed by connection of the electrodes to a source of electrical energy, for example, a battery. If the integrin inhibitor to be delivered into the body is positively charged (i.e., a cation), then the anode will be the active electrode and the cathode will serve to complete the circuit. If the integrin inhibitor to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

Iontophoretic delivery devices can also be used to deliver an uncharged drug into the body. This is accomplished by a process called electroosmosis. Electroosmosis is the transdermal flux of a liquid solvent (e.g., the liquid solvent containing the uncharged drug or agent) which is induced by the presence of an electric field imposed across the skin by the donor electrode.

The iontophoresis device includes a drug or agent reservoir or source of the integrin inhibitor drug (which is preferably an ionized or ionizable form of the drug or a precursor of such drug) to be iontophoretically delivered or introduced into the body. Such drug reservoir is electrically connected to the anode or the cathode of the iontophoresis device to provide a fixed or renewable source of one or more desired integrin inhibitors.

A variety of iontophoresis patch designs may be suitably used in the present invention. For example, iontophoretic delivery devices have been developed in which the donor and counter electrode assemblies have a "multi-laminate" construction. In these devices, the donor and counter electrode assemblies are each formed by multiple layers of usually polymeric matrices. For example, U.S. Pat. No. 4,731,049 discloses a donor electrode assembly having a hydrophilic polymer based electrolyte reservoir and drug reservoir layers, a skin-contacting hydrogel layer, and optionally one or more semipermeable membrane layers. U.S. Pat. No. 4,474,570 discloses an iontophoresis device wherein the electrode assemblies include a conductive resin film electrode layer, a hydrophilic gel reservoir layer, and aluminum foil conductor layer and an insulating backing layer.

The drug and electrolyte reservoir layers of the iontophoretic delivery device may be, for example, formed of hydrophilic polymers, as described, for example, in U.S. Pat. Nos. 4,474,570, 4,383,529, 4,764,164. Hydrophilic polymers may be desired since water is the preferred solvent for ionizing many drug salts, and hydrophilic polymer components of the drug reservoir in the donor electrode and the electrolyte reservoir in the counter electrode can be hydrated in situ while attached to the body by absorbing water from the skin through transepidermal water loss or sweat or from a mucosal membrane by absorbing saliva in the case of oral mucosal membranes. Once hydrated, the device begins to deliver ionized agent to the body. This enables the drug reservoir to be manufactured in a dry state, giving the device a longer shelf life. Hydrogels have been particularly favored for use as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes.

The present invention provides improved methods for the delivery of integrin antagonists. Preferred in the present invention are inhibitors of the IIb/IIIa integrin and inhibitors of the $\alpha_v\beta_3$ integrin.

Inhibitors of the integrin IIb/IIIa useful as therapeutic antithrombotic agents. IIb/IIIa antagonists bind to IIb/IIIa on the membrane of platelets. By binding to IIb/IIIa these agents prevent platelets from aggregating. Platelet aggregation is associated with various cardiovascular and cerebrovascular disorders, including unstable angina, myocardial infarction, stroke, and atherosclerosis. IIb/IIIa antagonists are useful in preventing platelet aggregation and thrombosis, and for the treatment, including prevention, of various cardiovascular and cerebrovascular disorders.

IIb/IIa antagonists have been found to have relatively steep dose versus response profiles. Thus, within a relatively narrow range of plasma concentrations, the effect of a IIb/IIIa receptor antagonist could vary from no anticoagulant effect, to partial inhibition of platelet aggregation, to excessive prolongation of coagulation. In addition, IIb/IIIa receptor antagonists may have relatively low to modest or variable oral bioavailability. Low and variable oral bioavailability may be associated with variability in plasma concentrations and poor control of pharmacologic and toxic responses. The controlled iontophoretic transdermal delivery methods of the present invention, provide methods for administering a IIb/IIIa antagonist at a constant, relatively low rate, thereby to provide plasma concentrations and effects that do not vary excessively with time or from patient-to-patient, and provide therapeutic advantages over methods of drug delivery that produce variable plasma concentrations and effects.

Another preferred aspect of this invention provides iontophoresis methods of pharmaceutical delivery of compounds which are antagonists of the $\alpha_v\beta_3$ integrin. Such compounds inhibit the binding of vitronectin or other RGD-containing ligands to $\alpha_v\beta_3$ and inhibit cell adhesion. The present invention also includes iontophoresis devices containing such $\alpha_v\beta_3$ inhibitor compounds and methods of using such devices for the inhibition of angiogenesis, the treatment of disorders mediated by angiogenesis, thrombosis, restenosis, and other diseases or conditions mediated by or involving cell adhesion and/or cell migration and/or angiogenesis, including, but not limited to, other thromboembolic disorders, inflammation, inflammatory bowel disease and other autoimmune diseases, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, cancer metastasis, wound healing, diabetic retinopathy, ocular vasculopathies, bone degradation, diabetic retinopathy, macular degeneration, and wound healing. As used herein, the term "treatment" of a disorder includes the prevention of such disorder.

Representative integrin inhibitor compounds, including IIb/IIIa inhibitors, which may be delivered iontophoretically in the method of the present invention are disclosed in the following patents and patent applications: PCT Patent Application 95/14683; copending, commonly assigned U.S. patent application Ser. No. 08/455,768 filed May 31, 1995; copending, commonly assigned U.S. patent application Ser. No. 08/449,597 filed May 24, 1995; copending, commonly assigned U.S. patent application Ser. No. 08/455,768 filed May 31, 1995; copending, commonly assigned U.S. patent application Ser. No. 60/009088 filed Dec 22, 1995; copending, commonly assigned U.S. patent application Ser. No. 60/013539 filed Mar. 15, 1996; PCT Patent Application 95/32710; U.S. Pat. No. 5,334,596; U.S. Pat. No. 5,276,049; U.S. Pat. No. 5,281,585; European Patent Application 478, 328; European Patent Application 478,363; European Patent Application 512,831; PCT Patent Application 94/08577; PCT Patent Application 94/08962; PCT Patent Application 94/18981; PCT Patent Application 93/16697; Canada Patent Application 2,075,590; PCT Patent Application 93/18057; European Patent Application 445,796; Canada Patent Application 2,093,770; Canada Patent Application 2,094,773; Canada Patent Application 2,101,179; Canada Patent Application 2,074,685; Canada Patent Application 2,094,964; Canada Patent Application 2,105,934; Canada Patent Application 2,114,178; Canada Patent Application 2,116,068; European Patent Application 513,810; PCT Patent Application 95/06038; European Patent Application 381,033; PCT Patent Application 93/07867; PCT Patent Application 94/02472.

In the present invention it has been discovered that integrin inhibitors, in particular inhibitors of the IIb/IIIa and $\alpha_v\beta_3$ integrins, are preferably delivered using an electrically powered iontophoretic delivery device. The present invention includes iontophoretic delivery devices comprising an integrin inhibitor and methods for using such devices for the treatment of diseases mediated by such integrin, which comprises iontophoretically administering to a host in need of such treatment a therapeutically effective amount of such integrin inhibitor.

The present invention also provides pharmaceutical compositions suitable for iontophoretic delivery comprising an integrin inhibitor and a pharmaceutically acceptable carrier.

[1] Preferred integrin inhibitor compounds useful in the iontophoretic devices and iontophoretic methods of the present invention are compounds of Formula I:

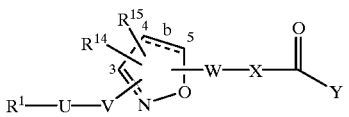

(I)

or a pharmaceutically acceptable salt form thereof wherein:

b is a carbon-carbon single or double bond;

$R^1$ is selected from $R^{2a}(R^3)N-$, $R^2(R^3)N(R^2N=)C-$, $R^{2a}(R^3)N(CH_2)_{p'}Z-$, $R^2(R^3)N(R^2N=)C(CH_2)_{p''}Z-$, $R^2(R^3)N(R^2N=)CN(R^2)-$, $R^2(R^3)NC(O)-$, $R^2(R^5O)N(R^2N=)C-$, $R^2(R^3)N(R^5ON=)C-$;

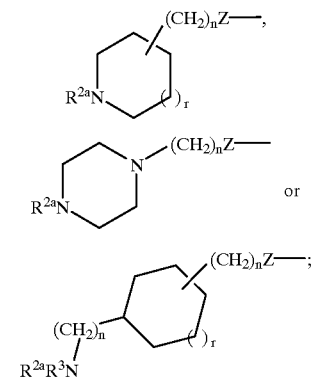

Z is selected from: a bond, O, S, S(=O), S(=O)$_2$;

$R^2$ and $R^3$ are independently selected from: H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; $C_2$–$C_7$ alkylcarbonyl; $C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; ($C_1$–$C_{10}$ alkoxy)carbonyl; $C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; aryl ($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; ($C_1$–$C_6$ alkyl)carbonyloxy($C_1$–$C_4$ alkoxy)carbonyl; ($C_6$–$C_{10}$ aryl)carbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; ($C_4$–$C_{11}$cycloalkylcarbonyl)oxy ($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; or heteroaryl ($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl;

provided that only one of $R^2$ and $R^3$ may be hydroxy;

$R^{2a}$ is $R^2$ or $R^2(R^3)N(R^2N=)C-$;

U is selected from:
  a single bond,
  $-(C_1-C_7$ alkyl$)-$,
  $-(C_2-C_7$ alkenyl$)-$,
  $-(C_2-C_7$ alkynyl$)-$;

V is selected from:
  a single bond;
  —($C_1$–$C_7$ alkyl)—, substituted with 0–3 groups independently selected from $R^6$ or $R^7$;
  —($C_2$–$C_7$ alkenyl)—, substituted with 0–3 groups independently selected from $R^6$ or $R^7$;
  —($C_2$–$C_7$ alkynyl)—, substituted with 0–3 groups independently selected from $R^6$ or $R^7$;
  —(phenyl)—Q—, said phenyl substituted with 0–2 groups independently selected from $R^6$ or $R^7$;
  —(pyridyl)—Q—, said pyridyl substituted with 0–2 groups independently selected from $R^6$ or $R^7$; or
  —(pyridazinyl)—Q—, said pyridazinyl substituted with 0–2 groups independently selected from $R^6$ or $R^7$, Q is selected from:
  a single bond,
  —O—, —S($°$)$_m$—, —N($R^{12}$)—, —($CH_2$)$_m$—,
  —C(=O)—,
  —N($R^{5a}$)C(=O)—, —C(=O)N($R^{5a}$)—, —$CH_2$O—,
  —O$CH_2$—,
  —$CH_2$N($R^{12}$)—, —N($R^{12}$)$CH_2$—, —$CH_2$C(=O)—,
  —C(=O)$CH_2$—,
  —$CH_2$S(O)$_m$—, or —S(O)$_m$$CH_2$—,
  provided that when b is a single bond, and $R^1$—U—V— is a substituent on C5 of the central 5-membered ring of Formula I, then Q is not —O—, —S(O)$_m$—, —N($R^{12}$)—, —C(=O)N($R^{5a}$)—, —$CH_2$O—, $CH_2$N($R^{12}$)— or —$CH_2$S(O)$_m$—;

W is selected from:
  —(C($R^4$)$_2$)$_{n'}$C(=O)N($R^{5a}$)— or —C(=O)—N($R^{5a}$)—(C($R^4$)$_2$)$_{n'}$—;

X is —(C($R^4$)$_2$)$_{n'}$—C($R^4$) ($R^8$)—C($R^4$) ($R^{4a}$)—;

Y is selected from hydroxy, $C_1$ to $C_{10}$ alkyloxy, $C_3$ to $C_{11}$ cycloalkyloxy, $C_6$ to $C_{10}$ aryloxy, $C_7$ $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, ($R^2$) ($R^3$)N—($C_1$–$C_{10}$ alkoxy)—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

alternately, two $R^4$ groups on adjacent carbon atoms may join to form a bond thereby to form a carbon-carbon double or triple bond between such adjacent carbon atoms;

$R^{4a}$ is selected from hydroxy, $C_1$–$C_{10}$ alkoxy, nitro, N($R^5$)$R^{5a}$, —N($R^{12}$)$R^{13}$, —N($R^{16}$)$R^{17}$, aryl substituted with 0–3 $R^6$, or ($C_1$–$C_{10}$ alkyl)carbonyl;

$R^{4b}$ is selected from H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —N($R^{12}$)$R^{13}$, halo, $CF_3$, CN, ($C_1$–$C_6$ alkoxy)carbonyl, carboxy, piperidinyl, morpholinyl or pyridinyl;

$R^5$ is selected from H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–6 $R^{4b}$;

$R^{5a}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^{4b}$;

alternately, $R^5$ and $R^{5a}$ when both are substituents on the same nitrogen atom (as in —NR$^5$R$^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl, ($C_7$–$C_{11}$ arylalkoxy)carbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, halo, $CF_3$, CHO, $CO_2R^5$, C(=O)$R^{5a}$, CONR$^5$R$^{5a}$, OC(=O)$R^{5a}$, OC(=O)OR$^{5b}$, OR$^{5a}$, OC(=O)NR$^5$R$^{5a}$, O$CH_2CO_2R^5$, $CO_2CH_2CO_2R^5$, $NO_2$, NR$^{5a}$C(=O) R$^{5a}$, NR$^{5a}$C(=O)OR$^{5b}$, NR$^{5a}$C(=O)NR$^5$R$^{5a}$, NR$^{5a}$SO$_2$NR$^5$R$^{5a}$, NR$^{5a}$SO$_2R^5$, S(O)$_m$R$^{5a}$, SO$_2$NR$^5$R$^{5a}$, SiMe$_3$, $C_2$ to $C_6$ alkenyl, $C_3$ to $C_{11}$ cycloalkyl, $C_4$ to $C_{11}$ cycloalkylmethyl;
  $C_6$ to $C_{10}$ aryl optionally substituted with 1–3 groups selected from halogen, $C_1$–$C_6$ alkoxy, $C_1$–$C_6$ alkyl, $CF_3$, S(O)$_m$Me, or —NMe$_2$;
  $C_7$ to $C_{11}$ arylalkyl, said aryl being optionally substituted with 1–3 groups selected from halogen, $C_1$–$C_6$ alkoxy, $C_1$–$C_6$ alkyl, $CF_3$, S(O)$_m$Me, or —NMe$_2$;
  methylenedioxy when $R^6$ is a substituent on aryl; or
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, halo, $CF_3$, CHO, $CO_2R^5$, C(=O)$R^{5a}$, CONR$^5$R$^{5a}$, OC(=O) R$^{5a}$, OC(=O)OR$^{5b}$, OR$^{5a}$, OC(=O)NR$^5$R$^{5a}$, O$CH_2CO_2R^5$, $CO_2CH_2CO_2R^5$, $NO_2$, NR$^{5a}$C(=O)R$^{5a}$, NR$^{5a}$C(=O)OR$^{5b}$, NR$^{5a}$C(=O)NR$^5$R$^{5a}$, NR$^{5a}$SO$_2$NR$^5$R$^{5a}$, NR$^{5a}$SO$_2R^5$, S(O)$_m$R$^{5a}$, SO$_2$NR$^5$R$^{5a}$, $C_2$ to $C_6$ alkenyl, $C_3$ to $C_1$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:
  $R^6$;
  $C_1$–$C_{10}$ alkyl, substituted with 0–3 $R^6$;
  $C_2$–$C_{10}$ alkenyl, substituted with 0–3 $R^6$;
  $C_2$–$C_{10}$ alkynyl, substituted with 0–3 $R^6$;
  $C_3$–$C_8$ cycloalkyl, substituted with 0–3 $R^6$;
  $C_5$–$C_6$ cycloalkenyl, substituted with 0–3 $R^6$;
  aryl, substituted with 0–3 $R^6$;
  5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl ($C_1$–$C_{10}$ alkyl)sulfonyl, arylsulfonyl, aryl ($C_2$–$C_{10}$ alkenyl) sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylc arbonyl, heteroarylsulfonyl, heteroarylalkylcarbonyl, or aryl ($C_1$–$C_{10}$ alkoxy)carbonyl, wherein said aryl groups are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, $CO_2R^5$ or —C(=O)N($R^5$)$R^{5a}$;

$R^{15}$ is selected from:
H; $R^6$; —$CO_2R^5$; —C(=O)N($R^5$)$R^{5a}$;
$C_1$–$C_{10}$ alkoxycarbonyl substituted with 0–2 $R^6$;
$C_1$–$C_{10}$ alkyl, substituted with 0–3 $R^6$;
$C_2$–$C_{10}$ alkenyl, substituted with 0–3 $R^6$;
$C_1$–$C_{10}$ alkoxy, substituted with 0–3 $R^6$;
aryl, substituted with 0–3 $R^6$; or
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;
provided that when b is a double bond, only one of $R^{14}$ or $R^{15}$ is present;

$R^{16}$ is selected from:
—C(=O)—O—$R^{18a}$,
—C(=O)—$R^{18b}$,
—C(=O) N($R^{18b}$)$_2$,
—C(=O)NHSO$_2R^{18a}$,
—C(=O) NHC(=O)$R^{18b}$,
—C(=O) NHC(=O)OR$^{18a}$,
—C(=O) NHSO$_2$NHR$^{18b}$,
—C(=S)—NH—$R^{18b}$,
—NH—C(=O)—O—$R^{18a}$,
—NH—C(=O)—$R^{18b}$,
—NH—C(=O)—NH—$R^{18b}$,
—SO$_2$—O—$R^{18a}$,
—SO$_2$—$R^{18a}$,
—SO$_2$—N($R^{18b}$)$_2$,
—SO$_2$—NHC(=O) OR$^{18b}$,
—P(=S) (OR$^{18a}$)$_2$,
—P(=O) (OR$^{18a}$)$_2$,
—P(=S) (R$^{18a}$)$_2$,
—P(=O) (R$^{18a}$)$_2$, or

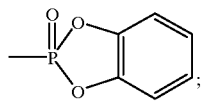

$R^{17}$ is selected from: H, $C_1$–$C_{10}$ alkyl, $C_2$–$C_6$ alkenyl, $C_3$–$C_{11}$, cycloalkyl, $C_4$–$C_{15}$ cycloalkylalkyl, aryl, aryl ($C_1$–$C_{10}$ alkyl)—;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a 5–10 membered heterocyclic ring system having 1–3 heteroatoms selected independently from O, S, and N, said heterocyclic ring being substituted with 0–4 $R^{19}$,
$C_1$–$C_6$ alkyl substituted with a 5–10 membered heterocyclic ring system having 1–3 heteroatoms selected independently from O, S, and N, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)—, $C_1$–$C_6$ alkoxy, heteroaryl, ($C_1$–$C_4$ alkyl) sulfonyl, aryl-sulfonyl, or $C_1$–$C_4$ alkoxycarbonyl;

m is 0–2;
n is 0–4;
n' is 0–4;
p' is 1–7;
p" is 1–7;
r is 0–3;
provided that n' are chosen such that the number of in-chain atoms connecting $R^1$ and Y is in the range of 8–18.

[2] Further preferred compounds useful in the present invention are compounds of claim 1 of Formula Ic:

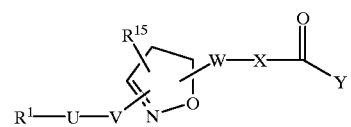

(Ic)

wherein:
$R^1$ is selected from $R^{2a}(R^3)$N—, $R^2(R^3)N(R^2N=)C$—, $R^{2a}(R^3)N(CH_2)_pZ$—, $R^2(R^3))N(R^2N=)C(CH_2)_p$-Z—, $R^2(R^3)N(R^2N=)CN(R^2)$—, $R^2(R^3)NC(O)$—, $R^2(R^5O)N(R^2N=)C$—, $R^2(R^3)N(R^5ON=)C$—;

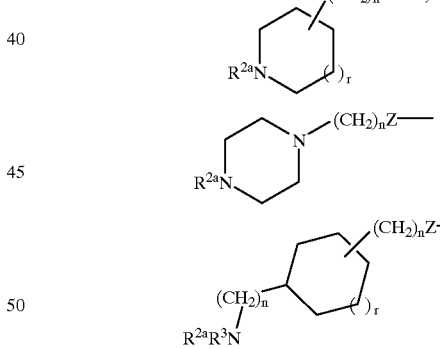

Z is selected from a bond, O, or S;
$R^2$ and $R^3$ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; ($C_1$–$C_{10}$ alkoxy)carbonyl; aryl($C_1$–$C_{10}$ alkoxy) carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_m CH_3$, —$N(CH_3)_2$, $C_1$–$C_4$ haloalkyl, methylenedioxydiyl, ethylenedioxydiyl;

$R^{2a}$ is $R^2$ or $R^2(R^3)N(R^2 N=)C$;

U is a single bond,

V is selected from:
  a single bond;
  —($C_1$–$C_7$ alkyl)—, substituted with 0–3 groups independently selected from $R^6$ or $R^7$;
  —($C_2$–$C_7$ alkenyl)—, substituted with 0–3 groups independently selected from $R^6$ or $R^7$;
  —($C_2$–$C_7$ alkynyl)—, substituted with 0–3 groups independently selected from $R^6$ or $R^7$;
  —(phenyl)—Q—, said phenyl substituted with 0–2 groups independently selected from $R^6$ or $R^7$;
  —(pyridyl)—Q—, said pyridyl substituted with 0–2 groups independently selected from $R^6$ or $R^7$; or
  —(pyridazinyl)—Q—, said pyridazinyl substituted with 0–2 groups independently selected from $R^6$ or $R^7$, Q is selected from
  a single bond,
  —O—, —$S(O)_m$—, —$N(R^{12})$—, —$(CH_2)_m$—,
  —$C(=O)$—,
  —$N(R^{5a})C(=O)$—, —$C(=O)N(R^{5a})$—, —$CH_2 O$—,
  —$OCH_2$—,
  —$CH_2 N(R^{12})$—, —$N(R^{12})CH_2$—, —$CH_2 C(=O)$—,
  —$C(=O)CH_2$—,
  —$CH_2 S(O)_m$—, or —$S(O)_m CH_2$—,
provided that when b is a single bond, and $R^1$—U—V— is a substituent on C5 of the central 5-membered ring of Formula Ic, then Q is not —O—, —$S(O)_m$—, —$N(R^{12})$—, —$C(=O)N(R^{5a})$—, —$CH_2 O$—, $CH_2 N(R^{12})$— or —$CH_2 S(O)_m$—;

W is selected from:
  —$(C(R^4)_2)$—$C(=O)$—$N(R^{5a})$— or —$C(=O)$—$N(R^{5a})$—$(C(R^4)2)$—;

X is —$C(R^4)(R^8)$—$CHR^{4a}$—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from hydroxy, $C_1$–$C_{10}$ alkoxy, nitro, —$N(R^5)R^{5a}$, —$N(R^{12})R^{13}$, or —$N(R^{16})R^{17}$, aryl substituted with 0–3 $R^6$, or ($C_1$–$C_{10}$ alkyl)carbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —$N(R^{12})R^{13}$, halo, $CF_3$, CN, ($C_1$–$C_6$ alkoxy)carbonyl, carboxy, piperidinyl, morpholinyl or pyridyl;

$R^5$ is selected from H or $C_1$–$C_{10}$ alkyl substituted with 0–6 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl, $C_1$–$C_{10}$ alkyl substituted with 0–2 $R^{4b}$;

alternately, $R^5$ and $R^{5a}$ can be taken together to be 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl or ($C_7$–$C_{11}$ arylalkoxy)carbonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$ Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$–$C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl)methyloxy;

$R^6$ and $R^7$ are each independently selected from H, $C_1$–$C_{10}$ alkyl, hydroxy, $C_1$–$C_{10}$ alkoxy, nitro, ($C_1$–$C_{10}$ alkyl)carbonyl, —$N(R^{12})R^{13}$, cyano, or halo;

$R^{12}$ and $R^{13}$ are each independently selected from H, $C_1$–$C_{10}$ alkyl, ($C_1$–$C_{10}$ alkoxy)carbonyl, (Cl-Clo alkyl) carbonyl, $C_1$–$C_{10}$ alkylsulfonyl, aryl($C_1$–$C_{10}$ alkyl)sulfonyl, arylsulfonyl, heteroarylsulfonyl, heteroarylcarbonyl, heteroarylalkylcarbonyl or aryl, wherein said aryl groups being optionally substituted with 0–3 substituents selected from the group consisting of: $C_1$–$C_4$ alkyl, $C_1$–$C_4$ alkoxy, halo, $CF_3$, and $NO_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, $CO_2 R^5$ or —$C(=O)N(R^5)R^{5a}$;

$R^{16}$ is selected from:
  —$C(=O)$—O—$R^{18a}$,
  —$C(=O)$—$R^{18b}$,
  —$C(=O)N(R^{18b})_2$,
  —$SO_2$—$R^{18a}$, or
  $SO_2$—$N(R^{18b})_2$;

$R^{17}$ is selected from: H or $C_1$–$C_5$ alkyl $R^{18a}$ is selected from:
  $C_1$–$C_8$ alkyl substituted with 0–2 $R^{19}$,
  $C_2$–$C_8$ alkenyl substituted with 0–2 $R^{19}$,
  $C_2$–$C_8$ alkynyl substituted with 0–2 $R^{19}$,
  $C_3$–$C_8$ cycloalkyl substituted with 0–2 $R^{19}$,
  aryl substituted with 0–4 $R^{19}$,
  aryl($C_1$–$C_6$ alkyl)-substituted with 0–4 $R^{19}$,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
  $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)—, ($C_1$–$C_4$ alkyl) sulfonyl, aryl-sulfonyl, or $C_1$–$C_4$ alkoxycarbonyl;

n is 0–4;
p' is 1–7;
p" is 1–7;
r is 0–3.

[3] Further preferred integrin inhibitor compounds useful in the present invention are compounds of Formula Ib:

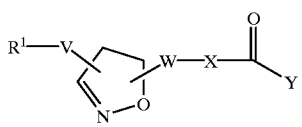
(Ib)

wherein:
$R^1$ is selected from: $R^{2a}(R^3)N$—, $R^2NH(R^2N=)C$—, $R^2NH(R^2N=)CNH$—, $R^{2a}(R^3)N(CH_2)_{p''}Z$—, $R^2NH(R^2N=)C(CH_2)_{p''}Z$—, $R^2(R^3)NC(O)$—, $R^2(R^5O)N(R^2N=)C$—, $R^2(R^3)N(R^5ON=)C$—;

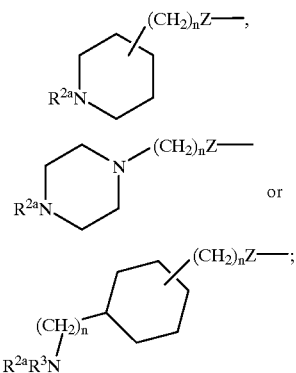

n is 0–1;
p' is 4–6;
p", is 2–4;
Z is selected from a bond or O;
V is a single bond, —(phenyl)— or —(pyridyl)—;
W is selected from:
—(C($R^4$)$_2$)—C(=O)—N($R^{5a}$)— or —C(=O)—N($R^{5a}$)—$CH_2$—;
X is selected from:
—$CH_2$—CH(N($R^{16}$)$R^{17}$)— or —$CH_2$—CH(N$R^5R^{5a}$)—;
Y is selected from:
hydroxy;
$C_1$ to $C_{10}$ alkoxy;
methylcarbonyloxymethoxy-;
ethylcarbonyloxymethoxy-;
t-butylcarbonyloxymethoxy-;
cyclohexylcarbonyloxymethoxy-;
1-(methylcarbonyloxy)ethoxy-;
1-(ethylcarbonyloxy)ethoxy-;
1-(t-butylcarbonyloxy)ethoxy-;
1-(cyclohexylcarbonyloxy)ethoxy-.;
i-propyloxycarbonyloxymethoxy-;
t-butyloxycarbonyloxymethoxy-;
1-(i-propyloxycarbonyloxy)ethoxy-;
1-(cyclohexyloxycarbonyloxy)ethoxy-;
1-(t-butyloxycarbonyloxy)ethoxy-;
dimethylaminoethoxy-;
diethylaminoethoxy-;
(5-methyl-1,3-dioxacyclopenten-2-on-4-yl)methoxy-;
(5-(t-butyl)-1,3-dioxacyclopenten-2-on-4-yl)methoxy-;
(1,3-dioxa-5-phenyl-cyclopenten-2-on-4-yl)methoxy-;
1-(2-(2-methoxypropyl)carbonyloxy)ethoxy-;

$R^{16}$ is selected from:
—C(=O)—O—$R^{18}$,
—C(=O)—$R^{18b}$,
—S(=O)$_2$—$R^{18a}$ or
—SO$_2$—N($R^{18b}$)$_2$;

$R^{17}$ is selected from H or $C_1$–$C_5$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)-substituted with 0–4 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
$C_1$–$C_6$ alkyl substituted with a heterocyclic ring system selected from pyridinyl, furanyl, thiazolyl, thienyl, pyrrolyl, pyrazolyl, imnidazolyl, isoxazolyl, isoxazolinyl, benzofuranyl, indolyl, indolenyl, quinolinyl, isoquinolinyl, benzimidazolyl, piperidinyl, tot rahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$.

[4] Further preferred compounds useful in the present invention are compounds of Formula Ic wherein:
$R^1$ is $R^2NH(R^2N=)C$— or $R^2HN(R^2N=)CNH$— and V is phenylene or pyridylene, or
$R^1$ is

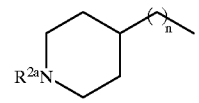

and V is a single bond;
n is 1 or 2;
$R^{18a}$ is selected from:
$C_1$–$C_4$ alkyl substituted with 0–2 $R^{19}$,
$C_2$–$C_4$ alkenyl substituted with 0–2 $R^{19}$,
$C_2$–$C_4$ alkynyl substituted with 0–2 $R^{19}$,
$C_3$–$C_7$ cycloalkyl substituted with 0–2 $R^{19}$,
aryl substituted with 0–4 $R^{19}$,
aryl ($C_1$–$C_4$ alkyl)—substituted with 0–4 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, isoxazolinyl or morpholinyl, said heterocyclic ring being substituted with 0–4 $R^{19}$;

$C_1$–$C_4$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, isoxazolinyl or morpholinyl, said heterocyclic ring being substituted with 0–4 $R^{19}$.

[5] Further preferred compounds useful in the present invention are compounds, or pharmaceutically acceptable salt forms thereof, selected from:

$N^3$-[2-{3-(4-formamidinophenyl)-isoxazolin-5(R,S)-yl}-acetyl]-N2-(phenylsulfonyl)-2,3-(S)-diaminopropanoic acid;

$N^3$-[2-{3-(4-formamidinophenyl)-isoxazolin-5(R,S)-yl}-acetyl]-N2-(4-methyl-phenyl-sulfonyl)-2,3-(S)-diaminopropanoic acid;

$N^3$-[2-{3-(4-formamidinophenyl)-isoxazolin-5(R,S)-yl}-acetyl]-N2-(butanesulfonyl)-2,3-(S)-diaminopropanoic acid;

$N^3$-[2-{3-(4-formamidinophenyl)-isoxazolin-5(R,S)-yl}-acetyl]-N2-(propanesulfonyl)-2,3-(S)-diaminopropanoic acid;

$N^3$-[2-{3-(4-formamidinophenyl)-isoxazolin-5(R,S)-yl}-acetyl]-N2-(ethanesulfonyl)-2,3-(S)-diaminopropanoic acid;

$N^3$-[2-{3-(4-formamidinophenyl)-isoxazolin-5(R,S)-yl}-acetyl]-N2-(methyloxycarbonyl)-2,3-(S)-diaminopropanoic acid;

$N^3$-[2-{3-(4-formamidinophenyl)-isoxazolin-5(R,S)-yl}-acetyl]-N2-(ethyloxycarbonyl)-2,3-(S)-diaminopropanoic acid;

$N^3$-[2-{3-(4-formamidinophenyl)-isoxazolin-5(R,S)-yl}-acetyl]-N2-(1-propyloxycarbonyl)-2,3-(S)-diaminopropanoic acid;

$N^3$-[2-{3-(4-formamidinophenyl)-isoxazolin-5(R,S)-yl}-acetyl]-N2-(2-propyloxycarbonyl)-2,3-(S)-diaminopropanoic acid;

$N^3$-[2-{3-(4-formamidinophenyl)-isoxazolin-5(R,S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(S)-diaminopropanoic acid;

$N^3$-[2-{3-(4-formamidinophenyl)-isoxazolin-5(S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(R)-diaminopropanoic acid;

$N^3$-[2-{3-(4-formamidinophenyl)-isoxazolin-5(S)-yl}-acetyl]-N2-(n-butyloxycarbonyl)-2,3-(R)-diaminopropanoic acid;

$N^3$-[2-{3-(4-formamidinophenyl)-isoxazolin-5(R,S)-yl}-acetyl]-N2-(2-butyloxycarbonyl)-2,3-(S)-diaminopropanoic acid;

$N^3$-[2-{3-(4-formamidinophenyl)-isoxazolin-5(R,S)-yl}-acetyl]-N2-(1-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(2-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(benzyloxycarbonyl)-2,3-(S)-diaminopropanoic acid;

$N^3$-[2-{3-(4-formamidinophenyl)-isoxazolin-5(R)-yl}-acetyl]-N2-(benzyloxycarbonyl)-2,3-(S)-diaminopropanoic acid;

$N^3$-[2-{3-(4-formamidinophenyl)-isoxazolin-5(S)-yl}-acetyl]-N2-(benzyloxycarbonyl)-2,3-(S)-diaminopropanoic acid;

$N^3$-[2-{3-(4-formamidinophenyl)-isoxazolin-5(R,S)-yl}-acetyl]-N2-(4-methylbenzyloxycarbonyl)-2,3-(S)-diaminopropanoic acid;

$N^3$-[2-{3-(4-formamidinophenyl)-isoxazolin-5(R,S)-yl}-acetyl]-N2-(4-methoxybenzyloxycarbonyl)-2,3-(S)-diaminopropanoic acid;

$N^3$-[2-{3-(4-formamidinophenyl)-isoxazolin-5(R,S)-yl}-acetyl]-N2-(4-chlorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-bromobenzyloxycarbonyl)-2,3-(S)-diaminopropanoic acid;

$N^3$-[2-{3-(4-formamidinophenyl)-isoxazolin-5(R,S)-yl}-acetyl]-N2-(4-fluorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-phenoxybenzyloxycarbonyl)-2,3-(S)-diaminopropanoic acid;

$N^3$-[2-{3-(4-formamidinophenyl)-isoxazolin-5(R,S)-yl}-acetyl]-N2-(2-(methyloxyethyl)-oxycarbonyl)-2,3-(S)-diaminopropanoic acid;

$N^3$-[2-{3-(4-formamidinophenyl)-isoxazolin-5(R,S)-yl}-acetyl]-N2-(2-pyridinylcarbonyl)-2,3-(S)-diaminopropanoic acid;

$N^3$-[2-{3-(4-formamidinophenyl)-isoxazolin-5(R,S)-yl}-5 acetyl]-N2-(3-pyridinylcarbonyl)-2,3-(S)-diaminopropanoic acid;

$N^3$-[2-{3-(4-formamidinophenyl)-isoxazolin-5(R,S)-yl}-acetyl]-N2-(4-pyridinyl-carbonyl)-2,3-(S)-diaminopropanoic acid;

$N^3$-[2-{3-(4-formamidinophenyl)-isoxazolin-5(R,S)-yl}-acetyl]-N2-(2-(2-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(3-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(4-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(3-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(4-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(4-butyloxyphenylsulfonyl)-2,3-(S)-diaminopropanoic acid;

N³-[2-{3-(4-formamidinophenyl)-isoxazolin-5(R,S)-yl}-acetyl]-N2-(2-thienylsulfonyl)-2,3-(S)-diaminopropanoic acid;

N³-[2-{3-(4-formamidinophenyl)-isoxazolin-5(R,S)-yl}-acetyl]-N2-(3-methylphenylsulfonyl)-2,3-(R,S)-diaminopropanoic acid;

N³-[2-{3-(4-formamidinophenyl)-isoxazolin-5(R,S)-yl}-acetyl]-N2-(3-methylphenylsulfonyl)-2,3-(S)-diaminopropanoic acid;

N³-[2-{3-(4-formamidinophenyl)-isoxazolin-5(R,S)-yl}-acetyl]-N2-(3-methylphenylsulfonyl)-2,3-(R)-diaminopropanoic acid;

N³-[2-{3-(4-formamidinophenyl)-isoxazolin-5(R)-yl}-acetyl]-N2-(3-methylphenylsulfonyl)-2,3-(S)-diaminopropanoic acid;

N³-[2-{3-(4-formamidinophenyl)-isoxazolin-5(S)-yl}-acetyl]-N2-(3-methylphenylsulfonyl)-2,3-(S)-diaminopropanoic acid;

N³-[2-{3-(4-formamidinophenyl)-isoxazolin-5(S)-yl}-acetyl]-N2-(3-methylphenylsulfonyl)-2,3-(R)-diaminopropanoic acid;

N³-[2-{3-(4-formamidinophenyl)-isoxazolin-5(R)-yl}-acetyl]-N2-(3-methylphenylsulfonyl)-2,3-(R)-diaminopropanoic acid;

N³-[2-{3-(4-formamidinophenyl)-isoxazolin-5(R,S)-yl}-acetyl]-N2-(4-iodophenylsulfonyl)-2,3-(S)-diaminopropanoic acid;

N³-[2-{3-(4-formamidinophenyl)-isoxazolin-5(R,S)-yl}-acetyl]-N2-(3-trifluoromethylphenylsulfonyl)-2,3-(S)-diaminopropanoic acid;

N³-[2-{3-(4-formamidinophenyl)-isoxazolin-5(R,S)-yl}-acetyl]-N2-(3-chlorophenylsulfonyl)-2,3-(S)-diaminopropanoic acid;

N³-[2-{3-(4-formamidinophenyl)-isoxazolin-5(R,S)-yl}-acetyl]-N2-(3–2-methoxycarbonylphenylsulfonyl)-2,3-(S)-diaminopropanoic acid;

N³-[2-{3-(4-formamidinophenyl)-isoxazolin-5(R,S)-yl}-acetyl]-N2-(2,4,6-trimethylphenylsulfonyl)-2,3-(S)-diaminopropanoic acid;

N³-[2-{3-(4-formamidinophenyl)-isoxazolin-5(R,S)-yl}-acetyll]-N2-(2-chlorophenylsulfonyl)-2,3-(S)-diaminopropanoic acid;

N³-[2-{3-(4-formamidinophenyl)-isoxazolin-5(R,S)-yl}-acetyl]-N2-(4-trifluoromethylphenylsulfonyl)-2,3-(S)-diaminopropanoic acid;

N³-[2-{3-(4-formamidinophenyl)-isoxazolin-5(R,S)-yl}-acetyl]-N2-(2-trifluoromethylphenylsulfonyl)-2,3-(S)-diaminopropanoic acid;

N³-[2-{3-(4-formamidinophenyl)-isoxazolin-5(R,S)-yl}-acetyl]-N2-(2-fluorophenylsulfonyl)-2,3-(S)-diaminopropanoic acid;

N³-[2-{3-(4-formamidinophenyl)-isoxazolin-5(R,S)-yl}-acetyl]-N2-(4-fluorophenylsulfonyl)-2,3-(S)-diaminopropanoic acid;

N³-[2-{3-(4-formamidinophenyl)-isoxazolin-5(R,S)-yl}-acetyl]-N2-(4-methoxyphenylsulfonyl)-2,3-(S)-diaminopropanoic acid;

N³-[2-{3-(4-formamidinophenyl)-isoxazolin-5(R,S)-yl}-acetyl]-N2-(2,3,5,6-tetramethylphenylsulfonyl)-2,3-(S)-diaminopropanoic acid;

N³-[2-{3-(4-formamidinophenyl)-isoxazolin-5(R,S)-yl}-acetyl]-N2-(4-cyanophenylsulfonyl)-2,3-(S)-diaminopropanoic acid;

N³-[2-{3-(4-formamidinophenyl)-isoxazolin-5(R,S)-yl}-acetyl]-N2-(4-chlorophenylsulfonyl)-2,3-(S)-diaminopropanoic acid;

N³-[2-{3-(4-formamidinophenyl)-isoxazolin-5(R,S)-yl}-acetyl]-N2-(4-propylphenylsulfonyl)-2,3-(S)-diaminopropanoic acid;

N³-[2-{3-(4-formamidinophenyl)-isoxazolin-5(R,S)-yl}-acetyl]-N2-(2-phenylethylsulfonyl)-2,3-(S)-diaminopropanoic acid;

N³-[2-{3-(4-formamidinophenyl)-isoxazolin-5(R,S)-yl}-acetyl]-N2-(4-isopropylphenylsulfonyl)-2,3-(S)-diaminopropanoic acid;

N³-[2-{3-(4-formamidinophenyl)-isoxazolin-5(R,S)-yl}-acetyl]-N2-(3-phenylpropylsulfonyl)-2,3-(S)-diaminopropanoic acid;

N³-[2-{3-(4-formamidinophenyl)-isoxazolin-5(R,S)-yl}-acetyl]-N2-(3-pyridylsulfonyl)-2,3-(S)-diaminopropanoic acid;

N³-[2-{3-(4-formamidinophenyl)-isoxazolin-5(R,S)-yl}-acetyl]-N2-(phenylaminosulfonyl)-2,3-(S)-diaminopropanoic acid;

N³-[2-{3-(4-formamidinophenyl)-isoxazolin-5(R,S)-yl}-acetyl]-N2-(benzylaminosulfonyl)-2,3-(S)-diaminopropanoic acid;

N³-[2-{3-(4-formamidinophenyl)-isoxazolin-5(R,S)-yl}-acetyl]-N2-(dimethylaminosulfonyl)-2,3-(S)-diaminopropanoic acid;

N³-[2-{3-(2-fluoro-4-formamidinophenyl)-isoxazolin-5(R,S)-yl}-acetyl]-N2-(3-methylphenylsulfonyl)-2,3-(S)-diaminopropanoic acid;

N³-[2-{3-(2-formamidino-5-pyridinyl)-isoxazolin-5(R,S)-yl}-acetyl]-N2-(n-butyloxycarbonyl)-2,3-(S)-diaminopropanoic acid;

N³-[2-{3-(2-formamidino-5-pyridinyl)-isoxazolin-5(R,S)-yl}-acetyl]-N2-(3-methylphenylsulfonyl)-2,3-(S)-diaminopropanoic acid;

N³-[2-{3-(3-formamidino-6-pyridinyl)-isoxazolin-5(R,S)-yl}-acetyl]-N2-(n-butyloxycarbonyl)-2,3-(S)-diaminopropanoic acid;

N³-[2-{3-(3-formamidino-6-pyridinyl)-isoxazolin-5(R,S)-yl}-acetyl]-N2-(3-methylphenylsulfonyl)-2,3-(S)-diaminopropanoic acid;

N³-[2-{3-(4-formamidinophenyl)-isoxazolin-5(R,S)-yl}-acetyl]-N2-(phenylaminocarbonyl)-2,3-(S)-diaminopropanoic acid;

N³-[2-{3-(4-formamidinophenyl)-isoxazolin-5(R,S)-yl}-acetyl]-N2-(4-fluorophenylaminocarbonyl)-2,3-(S)-diaminopropanoic acid;

N³-[2-{3-(4-formamidinophenyl)-isoxazolin-5(R,S)-yl}-acetyl]-N2-(1-naphthylaminocarbonyl)-2,3-(S)-diaminopropanoic acid;

N³-[2-{3-(4-formamidinophenyl)-isoxazolin-5(R,S)-yl}-acetyl]-N2-(benzylaminocarbonyl)-2,3-(S)-diaminopropanoic acid;

N³-[2-{3-(4-formamidinophenyl)-isoxazolin-5(R,S)-yl}-5 acetyl]-N2-(3-bromo-2-thienylsulfonyl)-2,3-(S)-diaminopropanoic acid;

N³-[2-{3-(4-formamidinophenyl)-isoxazolin-5(R,S)-yl}-acetyl]-N2-(3-methyl-2-benzothienylsulfonyl)-2,3-(S)-diaminopropanoic acid;

N³-[2-{3-(4-formamidinophenyl)-isoxazolin-5(R,S)-yl}-acetyl]-N2-(isobutyloxycarbonyl)-2,3-(S)-diaminopropanoic acid;

$N^3$-[2-{3-(4-formamidinophenyl)-isoxazolin-5(R)-yl}-acetyl]-N2-(isobutyloxycarbonyl)-2,3-(S)-diaminopropanoic acid;

$N^3$-[2-{3-(4-formamidinophenyl)-isoxazolin-5(S)-yl}-acetyl]-N2-(isobutyloxycarbonyl)-2,3-(S)-diaminopropanoic acid;

$N^3$-[2-{3-(4-formamidinophenyl)-isoxazolin-5(R,S)-yl}-acetyl]-N2-(2-cyclopropylethoxycarbonyl)-2,3-(S)-diaminopropanoic acid;

$N^3$-[2-{3-(4-formamidinophenyl)-isoxazolin-5(R)-yl}-acetyl]-N2-(2-cyclopropylethoxycarbonyl)-2,3-(S)-diaminopropanoic acid;

$N^3$-[2-{3-(4-formamidinophenyl)-isoxazolin-5(S)-yl}-acetyl]-N2-(2-cyclopropylethoxycarbonyl)-2,3-(S)-diaminopropanoic acid;

$N^3$-[2-{3-(4-guanidinophenyl)-isoxazolin-5(R,S)-yl}-acetyl]-N2-(n-butyloxycarbonyl)-2,3-(S)-diaminopropanoic acid;

$N^3$-[2-{3-(4-guanidinophenyl)-isoxazolin-5(R)-yl}-acetyl]-N2-(n-butyloxycarbonyl)-2,3-(S)-diaminopropanoic acid;

$N^3$-[2-{3-(4-guanidinophenyl)-isoxazolin-5(R)-yl}-acetyl]-N2-(3-methylphenylsulfonyl)-2,3-(S)-diaminopropanoic acid;

$N^3$-[2-{5-(4-formamidinophenyl)-isoxazolin-3(R,S)-yl}-acetyl]-N2-(n-butyloxycarbonyl)-2,3-(S)-diaminopropanoic acid;

or a propionate ester prodrug form of said compound, wherein the hydrogen of the hydroxy group of the diaminopropanoic acid moiety is substituted with a group selected from:
methyl;
ethyl;
isopropyl;
methylcarbonyloxymemethyl-;
ethylcarbonyloxymemethyl-;
t-butylcarbonyloxymemethyl-;
cyclohexylcarbonyloxymemethyl-;
1-(methylcarbonyloxy)emethyl-;
1-(ethylcarbonyloxy)emethyl-;
1-(t-butylcarbonyloxy)emethyl-;
1-(cyclohexylcarbonyloxy)emethyl-;
i-propyloxycarbonyloxymemethyl-;
cyclohexylcarbonyloxymemethyl-;
t-butyloxycarbonyloxymemethyl-;
1-(i-propyloxycarbonyloxy)emethyl-;
1-(cyclohexyloxycarbonyloxy)emethyl-;
1-(t-butyloxycarbonyloxy)emethyl-;
dimethylaminoemethyl-;
diethylaminoemethyl-;
(5-methyl-1,3-dioxacyclopenten-2-on-4-yl)memethyl-;
(5-(t-butyl)-1,3-dioxacyclopenten-2-on-4-yl)memethyl-;
(1,3-dioxa-5-phenyl-cyclopenten-2-on-4-yl)memethyl-;
1-(2-(2-methoxypropyl)carbonyloxy)ethyl-.

[6] Further preferred compounds useful in the present invention are compounds, or enantiomeric or diasteriomeric forms thereof, or mixtures of enantiomeric or diasteriomeric forms thereof, or a pharmaceutically acceptable salt form thereof, selected from:

$N^3$-[2-{3-(4-formamidinophenyl)-isoxazolin-5-yl}-acetyl]-$N^2$-(phenylsulfonyl)-2,3-diaminopropanoic acid;

$N^3$-[2-{3-(4-formamidinophenyl)-isoxazolin-5-yl}-acetyl]-$N^2$-(4-methyl-phenyl-sulfonyl)-2,3-diaminopropanoic acid;

$N^3$-[2-{3-(4-formamidinophenyl)-isoxazolin-5-yl}-acetyl]-$N^2$-(butanesulfonyl)-2,3-diaminopropanoic acid;

$N^3$-[2-{3-(4-formamidinophenyl)-isoxazolin-5-yl}-acetyl]-$N^2$-(propanesulfonyl)-2,3-diaminopropanoic acid;

$N^3$-[2-{3-(4-formamidinophenyl)-isoxazolin-5-yl}-acetyl]-$N^2$-(ethanesulfonyl)-2,3-diaminopropanoic acid;

$N^3$-[2-{3-(4-formamidinophenyl)-isoxazolin-5-yl}-acetyl]-$N^2$-(methyloxycarbonyl)-2,3-diaminopropanoic acid;

$N^3$-[2-{3-(4-formamidinophenyl)-isoxazolin-5-yl}-acetyl]-$N^2$-(ethyloxycarbonyl)-2,3-diaminopropanoic acid;

$N^3$-[2-{3-(4-formamidinophenyl)-isoxazolin-5-yl}-acetyl]-$N^2$-(1-propyloxycarbonyl)-2,3-diaminopropanoic acid;

$N^3$-[2-{3-(4-formamidinophenyl)-isoxazolin-5-yl}-acetyl]-$N^2$-(2-propyloxycarbonyl)-2,3-diaminopropanoic acid;

$N^3$-[2-{3-(4-formamidinophenyl)-isoxazolin-5-yl}-acetyl]-$N^2$-(n-butyloxycarbonyl)-2,3-diaminopropanoic acid;

$N^3$-[2-{3-(4-formamidinophenyl)-isoxazolin-5-yl}-acetyl]-$N^2$-(1-(2-methyl)-propyloxycarbonyl)-2,3-diaminopropanoic acid;

$N^3$-[2-{3-(4-formamidinophenyl)-isoxazolin-5-yl}-acetyl]-$N^2$-(2-(2-methyl)-propyloxycarbonyl)-2,3-diaminopropanoic acid;

$N^3$-[2-{3-(4-formamidinophenyl)-isoxazolin-5-yl}-acetyl]-$N^2$-(benzyloxycarbonyl)-2,3-diaminopropanoic acid;

$N^3$-[2-{3-(4-formamidinophenyl)-isoxazolin-5-yl}-acetyl]-$N^2$-(4-methylbenzyloxycarbonyl)-2,3-diaminopropanoic acid;

$N^3$-[2-{3-(4-formamidinophenyl)-isoxazolin-5-yl}-acetyl]-$N^2$-(4-methoxybenzyloxycarbonyl)-2,3-diaminopropanoic acid;

$N^3$-[2-{3-(4-formamidinophenyl)-isoxazolin-5-yl}-acetyl]-$N^2$-(4-chlorobenzyloxycarbonyl)-2,3-diaminopropanoic acid;

$N^3$-[2-{3-(4-formamidinophenyl)-isoxazolin-5-yl}-acetyl]-$N^2$-(4-bromobenzyloxycarbonyl)-2,3-diaminopropanoic acid;

$N^3$-[2-{3-(4-formamidinophenyl)-isoxazolin-5-yl}-acetyl]-$N^2$-(4-fluorobenzyloxycarbonyl)-2,3-diaminopropanoic acid;

$N^3$-[2-{3-(4-formamidinophenyl)-isoxazolin-5-yl}-acetyl]-$N^2$-(4-phenoxybenzyloxycarbonyl)-2,3-diaminopropanoic acid;

$N^3$-[2-{3-(4-formamidinophenyl)-isoxazolin-5-yl}-acetyl]-$N^2$-(2-(methyloxyethyl)-oxycarbonyl)-2,3-diaminopropanoic acid;

$N^3$-[2-{3-(4-formamidinophenyl)-isoxazolin-5-yl}-acetyl]-$N^2$-(2-pyridinylcarbonyl)-2,3-diaminopropanoic acid;

$N^3$-[2-{3-(4-formamidinophenyl)-isoxazolin-5-yl}-acetyl]-$N^2$-(3-pyridinylcarbonyl)-2,3-diaminopropanoic acid;

$N^3$-[2-{3-(4-formamidinophenyl)-isoxazolin-5-yl}-acetyl]-$N^2$-(4-pyridinyl-carbonyl)-2,3-diaminopropanoic acid;

N³-[2-{3-(4-formamidinophenyl)-isoxazolin-5-yl}-acetyl]-N²-(2-(2-pyridinyl)-acetyl)-2,3-diaminopropanoic acid;

N³-[2-{3-(4-formamidinophenyl)-isoxazolin-5-yl}-acetyl]-N²-(2-(3-pyridinyl)-acetyl)-2,3-diaminopropanoic acid;

N³-[2-{3-(4-formamidinophenyl)-isoxazolin-5-yl}-acetyl]-N²-(2-(4-pyridinyl)-acetyl)-2,3-diaminopropanoic acid;

N³-[2-{3-(4-formamidinophenyl)-isoxazolin-5-yl}-acetyl]-N²-(2-pyridyl-methyloxycarbonyl)-2,3-diaminopropanoic acid;

N³-[2-{3-(4-formamidinophenyl)-isoxazolin-5-yl}-acetyl]-N²-(3-pyridyl-methyloxycarbonyl)-2,3-diaminopropanoic acid;

N³-[2-{3-(4-formamidinophenyl)-isoxazolin-5-yl}-acetyl]-N²-(4-pyridyl-methyloxycarbonyl)-2,3-diaminopropanoic acid;

N³-[2-{3-(4-formamidinophenyl)-isoxazolin-5-yl}-acetyl]-N²-(4-butyloxyphenylsulfonyl)-2,3-diaminopropanoic acid;

N³-[2-{3-(4-formamidinophenyl)-isoxazolin-5-yl}-acetyl]-N²-(2-thienylsulfonyl)-2,3-diaminopropanoic acid;

N³-[2-{3-(4-formamidinophenyl)-isoxazolin-5-yl}-acetyl]-N²-(3-methylphenylsulfonyl)-2,3-diaminopropanoic acid;

N³-[2-{3-(4-formamidinophenyl)-isoxazolin-5-yl}-acetyl]-N²-(4-iodophenylsulfonyl)-2,3-diaminopropanoic acid;

N³-[2-{3-(4-formamidinophenyl)-isoxazolin-5-yl}-acetyl]-N²-(3-trifluoromethylphenylsulfonyl)-2,3-diaminopropanoic acid;

N³-[2-{3-(4-formamidinophenyl)-isoxazolin-5-yl}-acetyl]-N²-(3-chlorophenylsulfonyl)-2,3-diaminopropanoic acid;

N³-[2-{3-(4-formamidinophenyl)-isoxazolin-5-yl}-acetyl]-N²-(2-methoxycarbonylphenylsulfonyl)-2,3-diaminopropanoic acid;

N³-[2-{3-(4-formamidinophenyl)-isoxazolin-5-yl}-acetyl]-N²-(2,4,6-trimethylphenylsulfonyl)-2,3-diaminopropanoic acid;

N³-[2-{3-(4-formamidinophenyl)-isoxazolin-5-yl}-acetyl]-N²-(2-chlorophenylsulfonyl)-2,3-diaminopropanoic acid;

N³-[2-{3-(4-formamidinophenyl)-isoxazolin-5-yl}-acetyl]-N²-(4-trifluoromethylphenylsulfonyl)-2,3-diaminopropanoic acid;

N³-[2-{3-(4-formamidinophenyl)-isoxazolin-5-yl}-acetyl]-N²-(2-trifluoromethylphenylsulfonyl)-2,3-diaminopropanoic acid;

N³-[2-{3-(4-formamidinophenyl)-isoxazolin-5-yl}-acetyl]-N²-(2-fluorophenylsulfonyl)-2,3-diaminopropanoic acid;

N³-[2-{3-(4-formamidinophenyl)-isoxazolin-5-yl}-acetyl]-N²-(4-fluorophenylsulfonyl)-2,3-diaminopropanoic acid;

N³-[2-{3-(4-formamidinophenyl)-isoxazolin-5-yl}-acetyl]-N²-(4-methoxyphenylsulfonyl)-2,3-diaminopropanoic acid;

N³-[2-{3-(4-formamidinophenyl)-isoxazolin-5-yl}-acetyl]-N²-(2,3,5,6-tetramethylphenylsulfonyl)-2,3-diaminopropanoic acid;

N³-[2-{3-(4-formamidinophenyl)-isoxazolin-5-yl}-acetyl]-N²-(4-cyanophenylsulfonyl)-2,3-diaminopropanoic acid;

N³-[2-{3-(4-formamidinophenyl)-isoxazolin-5-yl}-acetyl]-N²-(4-chlorophenylsulfonyl)-2,3-diaminopropanoic acid;

N³-[2-{3-(4-formamidinophenyl)-isoxazolin-5-yl}-acetyl]-N²-(4-propylphenylsulfonyl)-2,3-diaminopropanoic acid;

N³-[2-{3-(4-formamidinophenyl)-isoxazolin-5-yl}-acetyl]-N²-(2-phenylethylsulfonyl)-2,3-diaminopropanoic acid;

N³-[2-{3-(4-formamidinophenyl)-isoxazolin-5-yl}-acetyl]-N²-(4-isopropylphenylsulfonyl)-2,3-diaminopropanoic acid;

N³-[2-{3-(4-formamidinophenyl)-isoxazolin-5-yl}-acetyl]-N²-(3-phenylpropylsulfonyl)-2,3-diaminopropanoic acid;

N³-[2-{3-(4-formamidinophenyl)-isoxazolin-5-yl}-acetyl]-N²-(3-pyridylsulfonyl)-2,3-diaminopropanoic acid;

N³-[2-{3-(4-formamidinophenyl)-isoxazolin-5-yl}-acetyl]-N²-(phenylaminosulfonyl)-2,3-diaminopropanoic acid;

N³-[2-{3-(4-formamidinophenyl)-isoxazolin-5-yl}-acetyl]-N²-(benzylaminosulfonyl)-2,3-diaminopropanoic acid;

N³-[2-{3-(4-formamidinophenyl)-isoxazolin-5-yl}-acetyl]-N²-(dimethylaminosulfonyl)-2,3-diaminopropanoic acid;

N³-[2-{3-(2-fluoro-4-formamidinophenyl)-isoxazolin-5-yl}-acetyl]-N²-(3-methylphenylsulfonyl)-2,3-diaminopropanoic acid;

N³-[2-{3-(2-formamidino-5-pyridinyl)-isoxazolin-5-yl}-acetyl]-N²-(n-butyloxycarbonyl)-2,3-diaminopropanoic acid;

N³-[2-{3-(2-formamidino-5-pyridinyl)-isoxazolin-5-yl}-acetyl]-N²-(3-methylphenylsulfonyl)-2,3-diaminopropanoic acid;

N³-[2-{3-(3-formamidino-6-pyridinyl)-isoxazolin-5-yl}-acetyl]-N²-(n-butyloxycarbonyl)-2,3-diaminopropanoic acid, N³-[2-{3-(3-formamidino-6-pyridinyl)-isoxazolin-5-yl}-acetyl]-N²-(3-methylphenylsulfonyl)-2,3-diaminopropanoic acid, N³-[2-{3-(4-formamidinophenyl)-isoxazolin-5-yl}-acetyl]-N²-(phenylaminocarbonyl)-2,3-diaminopropanoic acid;

N³-[2-{3-(4-formamidinophenyl)-isoxazolin-5-yl}-acetyl]-N²-(4-fluorophenylaminocarbonyl)-2,3-diaminopropanoic acid;

N³-[2-{3-(4-formamidinophenyl)-isoxazolin-5-yl}-acetyl]-N²-(1-naphthylaminocarbonyl)-2,3-diaminopropanoic acid;

N³-[2-{3-(4-formamidinophenyl)-isoxazolin-5-yl}-acetyl]-N²-(benzylaminocarbonyl)-2,3-diaminopropanoic acid;

N³-[2-{3-(4-formamidinophenyl)-isoxazolin-5-yl}-acetyl]-N²-(3-bromo-2-thienylsulfonyl)-2,3-diaminopropanoic acid;

N³-[2-{3-(4-formamidinophenyl)-isoxazolin-5-yl}-acetyl]-N²-(3-methyl-2-benzothienylsulfonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(2-cyclopropylethoxycarbonyl)-2,3-diaminopropanoic acid, $N^3$-[2-{3-(4-guanidinophenyl)-isoxazolin-5-yl}-acetyl]-$N^2$-(n-butyloxycarbonyl)-2,3-diaminopropanoic acid;

$N^3$-[2-{3-(4-guanidinophenyl)-isoxazolin-5-yl}-acetyl]-$N^2$-(3-methylphenylsulfonyl)-2,3-diaminopropanoic acid;

$N^3$-[2-{5-(4-formamidinophenyl)-isoxazolin-3-yl}-acetyl]-$N^2$-(n-butyloxycarbonyl)-2,3-diaminopropanoic acid;

$N^3$-[2-{3-(4-formamidinophenyl)-isoxazolin-5-yl}-acetyl]-$N^2$-(2-bromo-phenylsulfonyl)-2,3-diaminopropionic acid;

$N^3$-[2-{3-(4-formamidinophenyl)-isoxazolin-5-yl}-acetyl]-$N^2$-(2-methyl-phenylsulfonyl)-2,3-diaminopropionic acid;

$N^3$-[2-{3-(3-formamidino-6-pyridinyl)-isoxazolin-5-yl}-acetyl]-$N^2$-(3-methylphenylsulfonyl)-2,3-diaminopropionic acid;

$N^3$-[2-{3-(2-formamidino-5-pyridinyl)-isoxazolin-5-yl}-acetyl]-$N^2$-(3-methylphenylsulfonyl)-2,3-diaminopropionic acid;

$N^3$-[2-{3-(2-fluoro-4-formamidinophenyl)-isoxazolin-5-yl}-acetyl]-$N^2$-(3-methylphenylsulfonyl)-2,3-diaminopropionic acid;

$N^3$-[2-{3-(4-formamidinophenyl)-isoxazolin-5-yl}-acetyl]-$N^2$-(3-bromo-phenylsulfonyl)-2,3-diaminopropionic acid;

$N^3$-[2-{3-(4-formamidinophenyl)-isoxazolin-5-yl}-acetyl]-$N^2$-(4-bromo-phenylsulfonyl)-2,3-diaminopropionic acid;

or a propionate ester prodrug form of said compound, wherein the hydrogen of the hydroxy group of the propanoic acid moiety is substituted with a group selected from:
methyl;
ethyl;
isopropyl;
methylcarbonyloxymemethyl-;
ethylcarbonyloxymemethyl-;
t-butylcarbonyloxymemethyl-;
cyclohexylcarbonyloxymemethyl-;
1-(methylcarbonyloxy)emethyl-;
1-(ethylcarbonyloxy)emethyl-;
1-(t-butylcarbonyloxy)emethyl-;
1-(cyclohexylcarbonyloxy)emethyl-;
i-propyloxycarbonyloxymemethyl-;
cyclohexylcarbonyloxymemethyl-;
t-butyloxycarbonyloxymemethyl-;
1-(i-propyloxycarbonyloxy)emethyl-;
1-(cyclohexyloxycarbonyloxy)emethyl-;
1-(t-butyloxycarbonyloxy)emethyl-;
dimethylaminoemethyl-;
diethylaminoemethyl-;
(5-methyl-1,3-dioxacyclopenten-2-on-4-yl)memethyl-;
(5-(t-butyl)-1,3-dioxacyclopenten-2-on-4-yl) memethyl-;
(1,3-dioxa-5-phenyl-cyclopenten-2-on-4-yl) memethyl-;
1-(2-(2-methoxypropyl)carbonyloxy)emethyl-;
said enantiomeric and diasteriomeric forms being selected from:
(R,S), (R,S);
(R), (R,S);
(S), (R,S);
(R), (R);
(S), (R);
(R), (S);
(S), (S).

[7] Further preferred compounds useful in the present invention are the above compounds wherein the hydrogen of the hydroxy group of the diaminopropanoic acid moiety is substituted with a group selected from:
methyl;
ethyl;
isopropyl.

[8] Further preferred compounds useful in the present invention are the above compounds wherein the pharmaceutically acceptable salt form is selected from: acetate, methanesulfonate, hydrochloride, benzenesulfonate, or para-toluenesulfonate.

[9] Specifically preferred in the present invention is the compound, and pharmaceutically acceptable salt forms and propionate ester prodrug forms thereof, which is:

$N^3$-[2-{3-(4-formamidinophenyl)-isoxazolin-5(R)-yl}-acetyl]-$N^2$-(n-butyloxycarbonyl)-2,3-(S)-diaminopropanoic acid.

[10] Specifically preferred in the present invention is the compound, said compound being referred to herein as "Compound A" which is:

methyl-$N^3$-[2-{3-(4-formamidinophenyl)-isoxazolin-5(R)-yl}-acetyl]-$N^2$-(n-butyloxycarbonyl)-2,3-(S)-diaminopropionate methanesulfonate salt.

The above preferred compounds useful in the present invention may be synthesized by one of skill in the art of organic synthesis using the methods described in PCT International Application Publication Number WO 95/14683 and WO 96/38426. In addition, Compound A may be synthesized by one of skill in art of organic synthesis using the procedures described in Zhang et al., *Tetrahedron Letters*, 37(26), 4455–58 (1996); Zhang et al., *J. Org. Chem.*, 62(8), 2469 (1997).

The present invention comprises methods for the treatment of thromboembolic disorders, said methods comprising iontophoretically administering to a host in need of such treatment a therapeutically effective amount of a compound described above.

The present invention also comprises methods of administering an integrin inhibitor compound, said methods comprising iontophoretically administering to a patient in need of such administration a therapeutically effective amount of such integrin inhibitor using an iontophoresis device comprising an integrin inhibitor compound as described above.

The present invention also comprises methods for the treatment of thrombosis which comprise administering to a patient in need of such treatment a therapeutically effective amount of an integrin inhibitor using an iontophoresis device comprising an integrin inhibitor compound as described above.

The present invention also comprises methods of inhibiting the aggregation of blood platelets which comprise administering to a host in need of such inhibition a therapeutically effective amount of a IIb/IIIa inhibitor using an iontophoresis device comprising an integrin inhibitor compound as described above.

The present invention also comprises methods of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprise administering to a host in need of such treatment a therapeutically effective amount of an integrin inhibitor using an iontophoresis device comprising an integrin inhibitor compound as described above.

As used herein the term "angiogenic disorders" means conditions involving abnormal neovascularization, such as tumor metastasis and ocular neovascularization, including, for example, diabetic retinopathy, neovascular glaucoma, age-related macular degeneration, and retinal vein occlusion.

The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes.

The term "therapeutically effective amount" as used herein means an amount of an integrin inhibitor that when administered alone or in combination with an additional therapeutic agent to a cell or mammal is effective to prevent or ameliorate the specified disease condition or the progression of the disease.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, $C_0$–$C_{10}$ denotes alkyl having 0 to 10 carbon atoms; thus, $C_0$ denotes a direct bond between the groups linked by the $C_0$ group); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocyclic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "prodrugs" refer to any covalently bonded carriers which release the active parent drug in vivo when such prodrug is administered to a mammalian subject. Prodrugs of the integrin inhibitor compounds specified herein are prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds, and the like.

As used herein, "pharmaceutically acceptable salts" refer to derivatives of the disclosed compounds wherein the parent compound is modified by making acid or base salts of the compound. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the compounds useful in the present invention include the conventional non-toxic salts or the quaternary ammonium salts of the compounds, formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds of the present invention which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

Pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The iontophoretic device useful in the present invention may, by way of example and not limitation, include the following component and materials.

A. Current Distributing Member/Active Electrode

The iontophoretic electrode of the invention includes a current distributing member which conveys electrical current into the iontophoretic reservoirs for the delivery of an ionized substance. The current distributing member is constructed of any of a large variety of electrically conductive materials, including both inert and sacrificial materials.

Inert conductive materials are those electrically conductive materials which, when employed in the iontophoretic devices of the invention, do not themselves undergo or participate in electrochemical reactions. Thus, an inert material distributes without being eroded or depleted due to the distribution of current, and conducts current through the generating hydronium or hydroxyl ions by, respectively, either reduction or oxidation of water. Inert conductive materials typically include, for example, stainless steel, platinum, gold, and carbon or graphite.

Alternatively, the current distributing member may be constructed from a sacrificial conductive material. A material may be considered sacrificial if, when employed as an electrode in an iontophoretic device of the invention, material is eroded or depleted due to its oxidation or reduction. Such erosion or depletion occurs when the materials and formulations used in the iontophoresis device enable a specific electrochemical reaction, such as when a silver electrode is used with a formulation containing chloride ions. In this situation, the current distributing member would not cause electrolysis of water, but would itself be oxidized or reduced.

Typically, for anodes, a sacrificial material would include an oxidizable metal such as silver, zinc, copper, etc. In contrast to the hydroxyl and hydronium ions electrochemically generated via an inert material, the ions electrochemically generated via a sacrificial material would include metal cations resulting from oxidation of the metal. Metal/metal salt anodes may also be employed. In such cases, the metal would oxidize to metal ions, which would then be precipitated as an insoluble salt.

For cathodes, the current distributing member may be constructed from any electrically conductive material provided an appropriate electrolyte formulation is provided. For example, the cathodic current distributing member may be constructed from a metal/metal salt material. A preferred cathodic material is a silver/silver halide material. In such embodiments, a metal halide salt is preferably employed as the electrolyte. In this case, the device would electrochemically generate halide ions from the electrode as the metal is reduced. Also, accompanying silver ions in a formulation would be reduced to silver metal and would deposit (plate) onto the electrode. In other embodiments, the cathode material may be an intercalation material, an amalgam, or other material which can take electrolyte cations such as sodium out of solution, below the reduction potential of water. In addition, other materials may be used which permit the plating out of a metal from the appropriate eletrolyte solution. Thus, metals such as silver, copper, zinc, and nickel, and other materials, such as carbon, may be employed when an appropriate metal salt such as silver nitrate or zinc sulfate is in solution in the electrolyte reservoir. While such materials may develop increased resistivity as a metal plates out during use, they are not eroded or depleted during use as cathodic current distributing members. They are therefore not strictly "sacrificial" in this context. Nonetheless, the term sacrificial encompasses such materials and is intended to include materials that undergo physical and/or chemical changes during iontophoresis.

The current distributing member may take any form known in the art, such as the form of a plate, foil layer, screen, wire, or dispersion of conductive particles embedded in a conductive matrix.

B. The Electrolyte Reservoir

In the iontophoretic devices of the invention, an electrolyte reservoir is arranged in electrical communication with a current distributing member. Typically, electrical communication requires that electrons from the current distributing member are exchanged with ions in the electrolyte reservoir upon the application of electrical current. Such electrical communication is preferably not impeded to any excessive degree by any intervening material(s) used in the construction of the iontophoretic device. In other words, the resistivity of the interface is preferably low.

The electrolyte reservoir comprises at least one electrolyte, i.e., an ionic or ionizable component which can act to conduct current toward or away from the current distributing member. Typically, the electrolyte comprises one or more mobile ions, the selection of which is dependent upon the desired application. Examples of suitable electrolytes include aqueous solutions of salts. A preferred electrolyte is an aqueous solution of NaCl, having a concentration of less than 1 mole/liter (<1 mM), more preferably at about physiological concentration. Other electrolytes include salts of physiological ions including, but not limited to, potassium, chloride, and phosphate. The salt and its concentration may be selected as desired for particular applications.

Other chemical species may be selected by the skilled artisan for inclusion in the electrolyte reservoir. Such other reservoir species include, without limitation, chelation agents (e.g., citrate ions, EDTA) surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulosic resins, clays), and the like.

Alternatively, the electrolyte may comprise a material which is itself relatively immobile in the absence of an electric field, but which acts to deliver mobile ions in the presence of an electric field. In the latter case, the electrolyte may more properly be termed an "ion source." Examples of ion sources according to the invention include polyelectrolytes, ion exchange membranes and resins, non-ionic buffers which become ionic upon pH change, and other known ion sources.

Alternatively, the electrolyte reservoir may contain counterions that form a soluble salt with an electrochemically generated ion. For example, in an apparatus employing a silver anodal current distributing member, a suitable counterion might be acetate or nitrate. Such counterions are useful when other means are provided for sequestering electrochemically generated ions.

Thus, the electrolyte reservoir can provide at least one ion of the same charge as the electrochemically generated ion, to permit current to be conducted, and at least one oppositely charged ion.

C. Agent Reservoir

The reservoir structure of the iontophoretic apparatus of the invention further includes an agent reservoir. The agent reservoir must be capable of ionic communication with an epithelial surface and is in electrical communication with the anode or cathode of the iontophoresis device.

The construction of the ionized substance reservoir must be consistent with the requirements for ionic communication with the epithelial surface and electrical communication with current distribution member. Accordingly, the structure of the ionized substance reservoir would vary, depending upon the desired application. The ionized substance reservoir may include a liquid, semi-liquid, semi-solid, or solid material. With a flowable material, the ionized substance reservoir preferably further comprises means for at least substantially inhibiting the flow of the contents out of the reservoir preferably further comprises means for at least substantially inhibiting the flow of the contents out of the reservoir. In such situations, the flow of the contents is desirably minimized when the device is in storage. For example, a membrane may be deployed to surround the contents of the ionized substance reservoir. In certain situations the flow of the contents of the reservoir may be minimized while in storage, but increased in use. For example, a surrounding membrane may increase in porosity, permeability, or conductivity upon the application of an electric field across the membrane. Examples of such membranes are disclosed in U.S. Pat. Nos. 5,080,546; 5,169,382;

and 5,232,438, the disclosures of which are incorporated by reference herein.

In preferred embodiments, the ionized substance reservoir is constructed to retain its physical integrity and to inherently resist migration and loss of the ionized substance. Such embodiments include those in which the ionized substance reservoir includes a solid or semi-solid material such as a gel or other polymeric material. In an especially preferred embodiment, the ionized substance reservoir includes a polymeric film in which the substance to be iontophoretically delivered is dispersed. The mobility of the substance to be delivered is substantially increased by the application of the electric field, permitting effective delivery across the target epithelial surface. Such a film need not contain any significant amount of hydrating material. In preferred embodiments, a cross-linked hydrogel in the electrolyte reservoir, because it inherently contains significant amounts of water, can server as a water reservoir during iontophoresis.

It may be desirable to provide the solution of active ingredient with a buffer. The ion of the buffer of like charge to the drug ion should have low ionic mobility. The limiting ionic mobility of this ion is preferably no greater than $1 \times 10^{-4}$ cm$^2$/volt-sec.

Additionally, it may be desirable to control the flux profile of the drug being delivered by iontophoresis by adding to or having present in the reservoir containing the drug, ions which would compete with the drug ions for current (competing ions). To achieve various flux profiles for the drug being iontophoretically delivered, one may apply constant current but vary the concentration of the competing ions.

D. Ionizable Substance (Drug) for Iontophoretic Delivery

The ionizable drug can be delivered from either the anode, the cathode, or both simultaneously. For example, if the compound to be driven into the body is positively charged, then the positive electrode (anode) will be the active electrode and the negative electrode (cathode) will serve to complete the electrochemical circuit. Alternatively, if the ionic substance to be delivered is negatively charged, then the negative electrode (cathode) will be the active electrode and the positive electrode (anode) will be the indifferent electrode.

It is believed that this invention has utility in connection with the delivery of active ingredients within the broad class of cell adhesion molecules as well as chemical modifications of cell adhesion molecules.

E. Protective Backing

The iontophoretic apparatus of the invention may also include a suitable backing film positioned on top of the electrolyte reservoir. The backing film provides protection against contamination and damage to the current distributing member, if present, and the electrolyte reservoir of the apparatus.

F. Release Liner

The iontophoretic apparatus of the invention optionally includes a release liner which may be fixed to the underside of the ionized substance reservoir by an adhesive. The release liner protects the surface of the ionized substance reservoir which contact the epithelial surface from contamination and damage when the device is not in use. When the device is ready for use, the release liner may be peeled off to expose the epithelial contacting surface of the ionized substance reservoir for application of the device to a patient.

G. Indifferent Electrode

Iontophoretic devices require at least two electrodes to provide a potential to drive drug ions into the skin of a patient. Both electrodes are disposed to be in intimate electrical contact with the skin thereby completing the electrochemical circuit formed by the anode pad and cathode pad of the iontophoretic device. The electrode pads may be further defined as an active electrode from which an ionic drug is delivered into the body. An indifferent or ground electrode serves to complete the electrochemical circuit.

FIG. 1 further illustrates the iontophoretic device useful in the present invention. FIG. 1 shows a schematic depiction of an embodiment of the iontophoretic device of this invention 50. An anode patch 10, having an anode electrode compartment 11 in ionic communication with a skin contacting compartment 13. The skin contacting compartment 13 and the anode electrode compartment 11 are separated by a compartment separation means (membrane) 17. The anode electrode compartment 11 also contains an anode 14 and an electrolyte (anolyte) 15. The skin contacting compartment is attached to the patient's skin 36. A cathode patch 20, having a cathode electrode compartment 21 in ionic communication with a skin contacting compartment 23. The skin contacting compartment 23 and the cathode electrode compartment 21 maybe separated by a compartment separation means (membrane) 27. The cathode electrode compartment 21 also contains a cathode 24 and an electrolyte (catholyte) 25. The skin contacting compartment is attached to the patient's skin 36.

The method and device of the present invention may, by way of example and not limitation, be used to administer a cell adhesion molecule to a patient during coronary angioplasty and for the treatment of diseases associated with abnormal platelet aggregation, thrombosis, rheumatoid arthritis, osteoporosis, restenosis, cancer metastasis, asthma, organ transplantation, septic shock, osteoarthritis, diabetes retinopathy, inflammatory bowel disease and artherosclerosis.

Applicants have recognized that some cell adhesion molecules are zwitterions, they have no net charge, they are electrically neutral, and in order to deliver the molecule across the skin in adequate quantity, it must have a net charge. Therefore, it is recognized that the molecules may need to be modified in order to deliver them iontophoretically. Such modification may be accomplished through process and methods known to those of ordinary skill in the art, by way of example and not limitation, such modification may be accomplished by esterification of the molecule, addition or deletion of amino acids.

The disclosures of all of the references cited herein are hereby incorporated herein by reference in their entirety.

Utility

The integrin inhibitor compounds delivered by iontophoresis in accordance with the present invention possess activity as antagonists of integrins such as, for example, IIb/IIIa, $\alpha_v\beta_3$, $\alpha_v\beta_5$ and $\alpha_5\beta_1$, and as such have utility in the treatment of a variety of disease conditions as discussed herein. The integrin antagonist activity of the compounds iontophoretically delivered in the present invention may be demonstrated using assays which measure the binding of a specific integrin to a native ligand, for example, using the ELISA assay described below for the binding of vitronectin to the $\alpha_v\beta_3$ receptor, or for example, an ELISA assay for the binding of fibrinogen to the IIb/IIIa receptor.

Compounds useful in the present invention include those that possess selectivity for the $\alpha_v\beta_3$ receptor relative to the IIb/IIIa receptor as demonstrated by their lack of activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The integrin inhibitor compounds iontophoretically delivered in the present invention are useful for the treatment or prevention of thromboembolic disorders and other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The $\alpha_v\beta_3$ integrin inhibitor compounds used in this invention have the ability to suppress/inhibit angiogenesis in vivo, for example, as demonstrated using =animal models of ocular neovascularization.

The IIb/IIIa inhibitor compounds used in this invention possess antiplatelet efficacy, as evidenced by their activity in standard platelet aggregation assays or platelet fibrinogen binding assays, as described below.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta)—Vitronectin ELISA, $\alpha_{v\beta3}$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 $\mu M$ for the inhibition of $\alpha_v\beta_3$-Vitronectin Binding Assay, with compounds preferably having $K_i$ values of less than about 0.1 $\mu M$. Tested compounds of the present invention are active in the $\alpha_{v3}$-Vitronectin Binding Assay.

Purified $\alpha_v\beta_3$ (human placenta)—Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\beta_v\beta_3$ or $\alpha_v\beta_5$ in the ELISA.

A submaximal concentration of biotinylated vitronectin was selected based on conc. response curve with fixed receptor conc. and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM $CaCl_2$, 1.0 mM $MgCl_2$. $6H_2O$, 1.0 mM $MnCl_2$. $4H_2O$) and coated (100 $\mu L$/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM $CaCl_2$,1.0 mM $MgCl_2$. $6H_2O$,1.0 mM $MnCl_2$. $4H_2O$). Receptor is then blocked (200 $\mu L$/well) with 3.5% BSA in B/B buffer for 2 hours at room temperature. After washing once with 1.0% BSA in B/B buffer, biotinylated vitronectin (100 $\mu L$) and either inhibitor (11 $\mu L$) or B/B buffer w/1.0% BSA (11 $\mu L$)is added to each well. The plates are incubated 2 hours at room temperature. The plates are washed twice with B/B buffer and incubated 1 hour at room temperature with anti-biotin alkaline phosphatase (100 $\mu L$/well) in B/B buffer containing 1.0% BSA. The plates are washed twice with B/B buffer and alkaline phosphatase substrate (100 $\mu L$) is added. Color is developed at room temperature. Color development is stopped by addition of 2N NaOH (25 $\mu L$/well) and absorbance is read at 405 nm. The $IC_{50}$ is the concentration of test substance needed to block 50% of the vitronectin binding to the receptor.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 $\mu L$ of PRP (5×$10^8$ platelets/mL) were added to each micro test tube, and transmittance was set to 0%. 20 $\mu L$ of ADP (10 $\mu M$) was added to each tube, and the aggregation profiles were plotted (% transmittance versus time). Test agent (20 $\mu L$) was added at different concentrations prior to the addition of the platelet agonist. Results are expressed as % inhibition of agonist-induced platelet aggregation.

Purified GPIIb/IIIa-Fibrinogen Binding ELISA

The following reagents are used in the GPIIb/IIIa-fibrinogen binding ELISA:
    purified GPIIb/IIIa (148.8 $\mu$/mL);
    biotinylated fibrinogen (~1 mg/mL or 3000 nM);
    anti-biotin alkaline phosphatase conjugate (Sigma no. A7418);
    flat-bottom, high binding, 96-well plates (Costar Cat. no. 3590);

phosphatase substrate (Sigma 104) (40 mg capsules);
bovine serum albumin (BSA) (Sigma no. A3294);
Alkaline Phosphatase buffer −0.1 M glycine-HCl, 1 mM MgCl$_2$.6H$_2$O, 1 mM ZnCl$_2$, pH 10.4;
Binding buffer −20 mM Tris-HCl, 150 mM NaCl, 1 mM CaCl$_2$. 2H$_2$O, 0.02% NaN$_3$, pH 7.0;
Buffer A −50 mM Tris-HCl, 100 mM NaCl, 2 mM CaCl$_2$. 2H$_2$O, 0.02% NaN$_3$, pH 7.4;
Buffer A +3.5% BSA (Blocking buffer);
Buffer A +0.1% BSA (Dilution buffer);
2N NaOH.

The following method steps are used in the GPIIb/IIIa-fibrinogen binding ELISA:

Coat plates with GPIIb/IIIa in Binding buffer (125 ng/100 μL/well) overnight at 4° C. (Leave first column uncoated for non-specific binding). Cover and freeze plates at −70° C. until used. Thaw plate 1 hour at room temperature or overnight at 4° C. Discard coating solution and wash once with 200 μL Binding buffer per well. Block plate 2 hours at room temperature on shaker with 200μL Buffer A +3.5% BSA (Blocking buffer) per well. Discard Blocking buffer and wash once with 200 μL Buffer A +0.1% BSA (Dilution buffer) per well. Pipet 11 μL of test compound (10× the concentration to be tested in Dilution buffer) into duplicate wells. Pipet 11 μL Dilution buffer into non-specific and total binding wells. Add 100 μL Biotinylated fibrinogen (1/133 in Dilution buffer, final concentration=20 nM) to each well. Incubate plates for 3 hours at room temperature on a plate shaker. Discard assay solution and wash twice with 300 μL Binding buffer per well. Add 100 μL Anti-biotin alkaline phosphatase conjugate (1/1500 in Dilution buffer) to each well. Incubate plates for 1 hour at room temperature on plate shaker. Discard conjugate and wash twice with 300 μL Binding buffer per well. Add 100 μL Phosphatase substrate (1.5 mg/mL in Alkaline phosphatase buffer) to each well. Incubate plate at room temperature on shaker until color develops. Stop color development by adding 25 μL 2N NaOH per well. Read plate at 405 nm. Blank against non-specific binding (NSB) well. % Inhibition is calculated as 100−(Test Compound Abs/Total Abs)×100.

Platelet-Fibrinogen Binding Assay Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets (5×10$^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The 125I-fibrinogen bound to the activated platelets was separated from the free form by centrifugation and then counted on a gamma counter For an IC$_{50}$ evaluation, the test compounds were added at various concentrations prior to the activation of the platelets.

Thrombolytic Assay

The integrin inhibitor compounds used in the present invention may also possess thrombolytic efficacy, that is, they are capable of lysing (breaking up) already formed platelet-rich fibrin blood clots, and thus are useful in treating a thrombus formation, as evidenced by their activity in the tests described below. Venous blood was obtained from the arm of a healthy human donor who was drug-free and aspirin free for at least two weeks prior to blood collection, and placed into 10 mL citrated Vacutainer tubes. The blood was centrifuged for 15 minutes at 1500×g at room temperature, and platelet rich plasma (PRP) was removed. To the PRP was then added 1×10$^{−3}$ M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the IC$_{50}$ evaluation, the test compounds were added at various concentrations, and the percentage of lysis caused by the test compounds was calculated.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67: 519–528

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

Integrin inhibitor compounds are iontophoretically delivered in accordance with this invention by transdermal iontophoretic delivery to provide contact of the active agent with the agent's site of action, the desired integrin, in the body of a mammal.

They can be administered by any conventional iontophoresis means available for use in conjunction with pharmaceuticals, either as individual therapeutic agents or in a combination of therapeutic agents.

The dosage of the integrin inhibitor compounds administered will, of course, vary depending upon known factors, such as the pharmacodynamic characteristics of the particular agent; the age, health and weight of the recipient; the nature of the target integrin; the nature and extent of the symptoms; the kind of concurrent treatment; the frequency of treatment; and the effect desired. A daily dosage of active ingredient can be expected to be about 0.001 to 10 milligrams per kilogram of body weight.

Suitable pharmaceutical carriers are described in Remington's Pharmaceutical Sciences, Mack Publishing Company, a standard reference text in this field.

EXAMPLES

Example 1

In Vitro Excised Skin Delivery Experiments

The iontophoretic delivery of a representative GPIIb/IIIa inhibitor compound, Compound A, was carried out in a flow-through diffusion cell in vitro excised skin delivery system.

The transdermal patch design used in these studies included an absorbent drug reservoir with 2 cm² active area of skin contact and a volume of 0.3 mL. The drug reservoir compartment was separated from the electrode compartment by a semi-permeable membrane with a molecular weight cutoff of 100. The electrode compartment included a silver anion and a cation exchange media in a hydrogel matrix. The drug reservoir compartment was filled with dosing solution just before application to the skin. A silver-silver chloride mesh return cathode was located upstream of the polycarbonate flow-through cells. Freshly dermatomed (1 mm) porcine skin was mounted in the cells on a porous support polyethylene. The patches included an absorbent reservoir in contact with silver and silver chloride electrodes. They were dosed with aqueous solutions of the drug and then placed on top of the excised skin. The patches were secured by a spring loaded mechanism which maintained even pressure over the patch. The cells were "perfused" by means of a peristaltic pump which pulls receiver solution through them. Effluents from the cells were collected with a fraction collector. Flow rates were typically 0.25 mL/min. The receiver solution was an isotonic pH 7.4 buffered saline solution containing 10 mM HEPES, 100 mM NaCl, PEG 400, and a surfactant, Pluronic P-103. Iontophoresis current was provided by a constant current power supplies, and the applied currents and cell voltages were recorded with a data logger.

The flux profile vs. time and the cumulative dose delivered with 18 hours of iontophoresis were determined. This was followed by 3 hours where no current was applied. Concentrations of Compound A were determined using a radiolabeled marker or by HPLC.

A study was performed using applied currents of 0–800 $\mu$A, and concentrations of Compound A in the patch of 50 or 100 mg/mL. A summary of the doses delivered is given in Table 1.

TABLE 1

Iontophoretic delivery of compound 1 through excised porcine skin in vitro. Each row represents an individual permeation experiment.

| Applied Current ($\mu$A) | Compound A Conc. (mg/mL, as salt) | Dose Delivered (mg) |
|---|---|---|
| 0 | 100 | 0.2 |
| 0 | 100 | 0.1 |
| 400 | 100 | 2.4 |
| 400 | 100 | 1.9 |
| 400 | 100 | 1.9 |
| 400 | 100 | 2.2 |
| 400 | 100 | 4.0 |
| 800 | 50 | 2.1 |
| 800 | 50 | 2.3 |
| 800 | 50 | 2.3 |
| 200 | 100 | 1.2 |
| 200 | 100 | 1.1 |
| 200 | 100 | 1.0 |
| 400 | 50 | 1.1 |
| 400 | 50 | 1.1 |
| 400 | 50 | 1.1 |

Results for the experiments in which there was no applied current indicate very low skin permeation. However, in the presence of the applied current the transdermal delivery of Compound A was greatly increased. The delivery profiles of flux vs time showed that delivery was maximum after about 5 hours of iontophoresis, after which the delivery rate was constant or slightly decreasing. The dosing rates were within the target range of 5–250 $\mu$g/hr. When the current was turned off the delivery rates fell to very low levels. These studies show that the delivery of Compound A at an optimal rate is possible through manipulation of the applied current or the concentration of the drug solution Furthermore, the delivery of Compound A by transdermal iontophoresis was generally very consistent for any specified drug concentration and applied current.

Additional studies were performed using lower applied currents, lower concentrations of Compound A in the patch, and dosing solutions containing various concentrations of NaCl. Transdermal delivery rates with dosing solutions containing 10 mg/mL Compound A and 154 mM NaCl were proportional to the applied current for currents of 0, 25, 50, and 100 $\mu$A. At 100 $\mu$A the delivery rate of Compound A was approximately 10 $\mu$g/hr for the 2 cm² surface area, which was also within the targeted range.

An alternative patch design, a monolithic patch rather than the membrane separated patch, was also tested. This patch is composed of two layers of absorbent material between which is sandwiched a silver anode. This monolithic patch provided similar profiles of transdermal iontophoretic delivery of compound 1 as the membrane separated patches.

Figure 2:
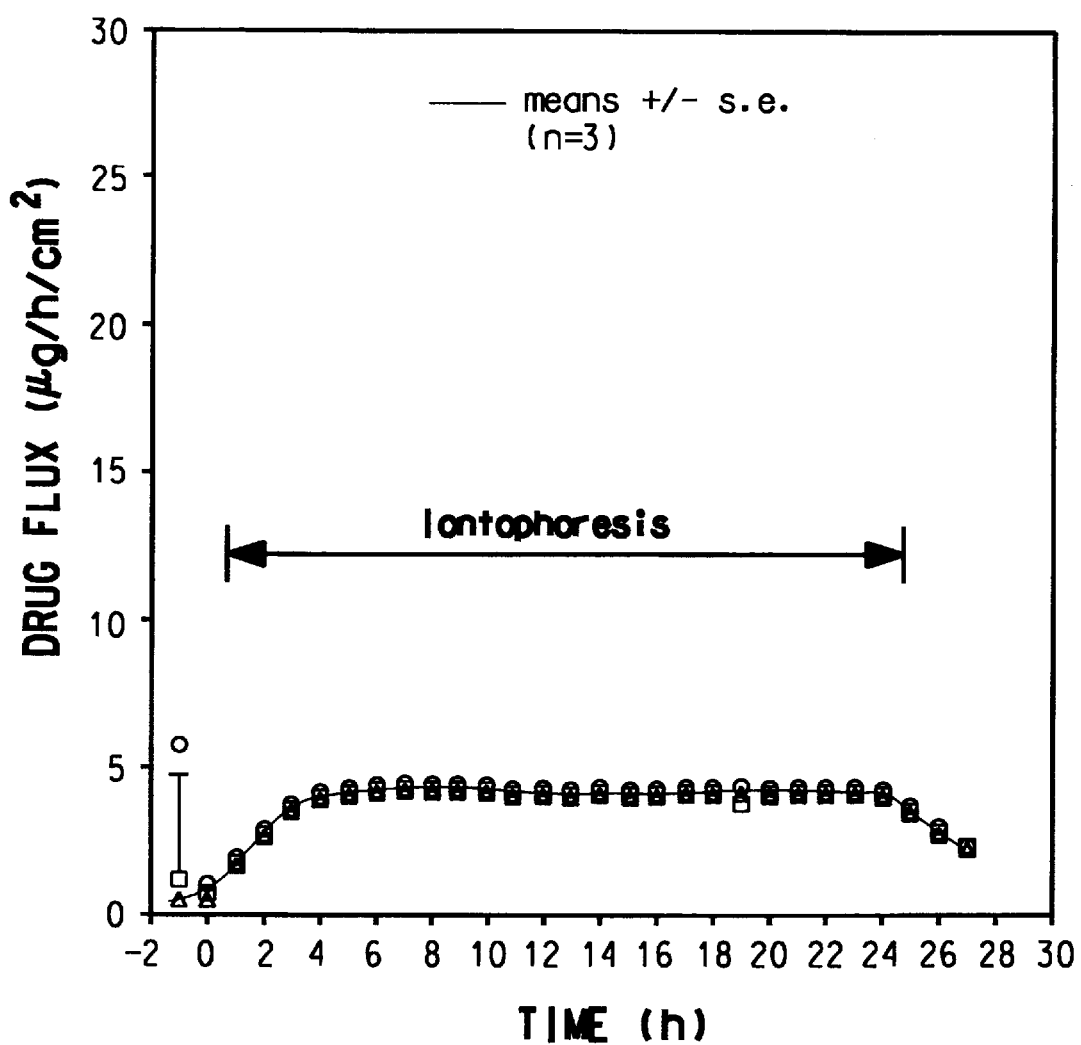
FIG. 2 shows the iontophoretic delivery across excised pig skin using a 2 cm$^2$ iontophoretic patch containing 10 mg/mL of Compound A and 154 mM NaCl at 50 $\mu$A.

FIG. 2 demonstrates that iontophoresis transport is a capable means for delivering Compound A to constant flux levels over a period of 24 hours. The variability in delivery from skin to skin is also extremely low.

Figure 3:
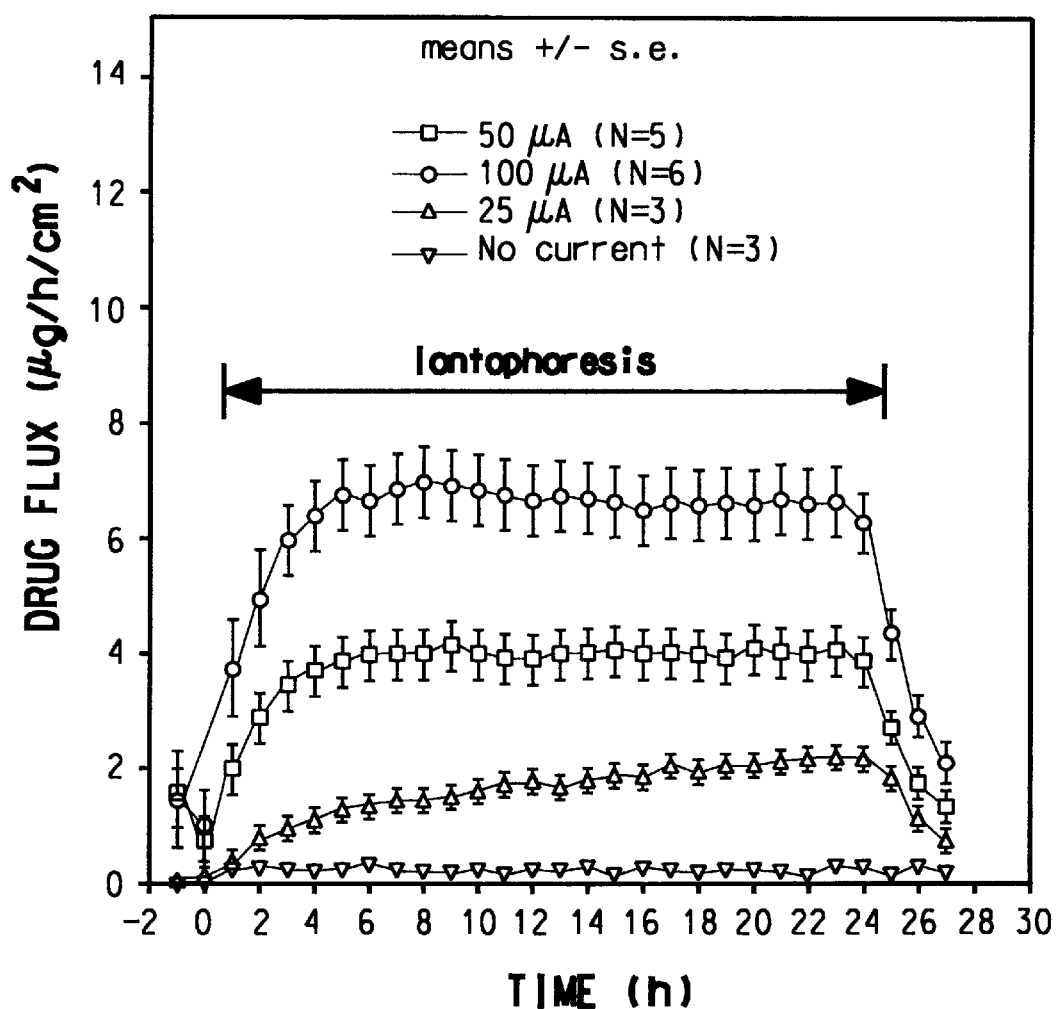
FIG. 3 shows the iontophoretic delivery across excised pig skin using a 2 cm$^2$ iontophoretic patch containing 10 mg/mL Compound A and 9 mg/mL NaCl at 0–100 $\mu$A.

FIG. 3 shows that the in vitro delivery is proportional to increase in current and that the flux is again very constant over the 24 hour period and between skin specimens as well. In these experiment the flux reaches "steady state" rapidly and it is also evident that flux levels drop rapidly on termination of the current. This latter feature is likely to be valuable in situations where the administration of the drug must be stopped rapidly to avoid a risk of harm or injury to the patient.

Example 2

In vivo Swine Experiments

The in vivo iontophoretic delivery of the representative integrin inhibitor Compound A was demonstrated using pigs. In each experiment, the patches were loaded with drug solution immediately before application to the skin of the animals. Unanesthetized Yorkshire swine with weights from about 20 to 35 kg were used. The skin sites receiving the patches were wiped clean with moist gauze pads. Patches were overwrapped with an adhesive, elastic wrap to hold the patches in place. Separate constant current power supplies were provided for each iontophoresis patch system. Current and voltage readings were made and recorded on-board dataloggers. Blood samples were withdrawn from the vena cava through an IV catheter into VACUTAINER™ blood collection tubes containing EDTA. After gentle mixing, the tubes were centrifuged to separate the plasma, which transferred to clean polypropylene tubes and frozen on dry ice. Frozen samples were stored at −80° C. until assayed.

In vivo, Compound A is rapidly converted to its acid form, $N^3$-[2-{3-(4-formamidinophenyl)-isoxazolin-5(R)-yl}-acetyl]-$N^2$-(n-butyloxycarbonyl)-2,3-(S)-diaminopropanoic acid (Compound B). Compound B concentrations in plasma were determined by LC-MS. The patches used were of the monolithic design described above, and having a 2 cm² skin coverage area. Patches were filled with solutions containing 10–20 mg/mL Compound A and 154 mM NaCl. Using a 20 mg/mL Compound A dosing solution, and an applied current of 100 $\mu$A, plasma concentrations of Compound B increased for the first 5–8 hours of dosing and then reached steady-state. Steady-state plasma concentrations of approximately 1–2 ng/mL were attained. After an intravenous infusion of Compound B at 10 µg/hr, steady-state plasma concentrations of Compound B were also approximately 1–2 ng/mL. Therefore, the transdermal delivery rate at steady-state was approximately 10 µg/hr.

Pigs were also dosed with patches containing 10 mg/mL of Compound A, using currents of 50 and 100 µA. In these studies four patches were used for each pig, for a total skin coverage area of 8 cm². Plasma concentrations of Compound B again increased over the first several hours of dosing and then reached an apparent steady-state. Transdermal iontophoretic dosing was maintained for 24 hours, during which plasma concentrations of Compound B were maintained fairly constant. Plasma concentrations were proportional to the applied current. Actual in vivo delivery rates were estimated by comparison with plasma concentrations after intravenous infusion of Compound B. The 50 µA current delivered Compound A at approximately 25 µg/hr, and the 100 µA current delivered Compound A at approximately 40 µg/hr. These results show that the in vivo continuous, controlled delivery of therapeutic doses of integrin receptor anagonists may be obtained using tranderdmal iontophoresis.

Figure 4:
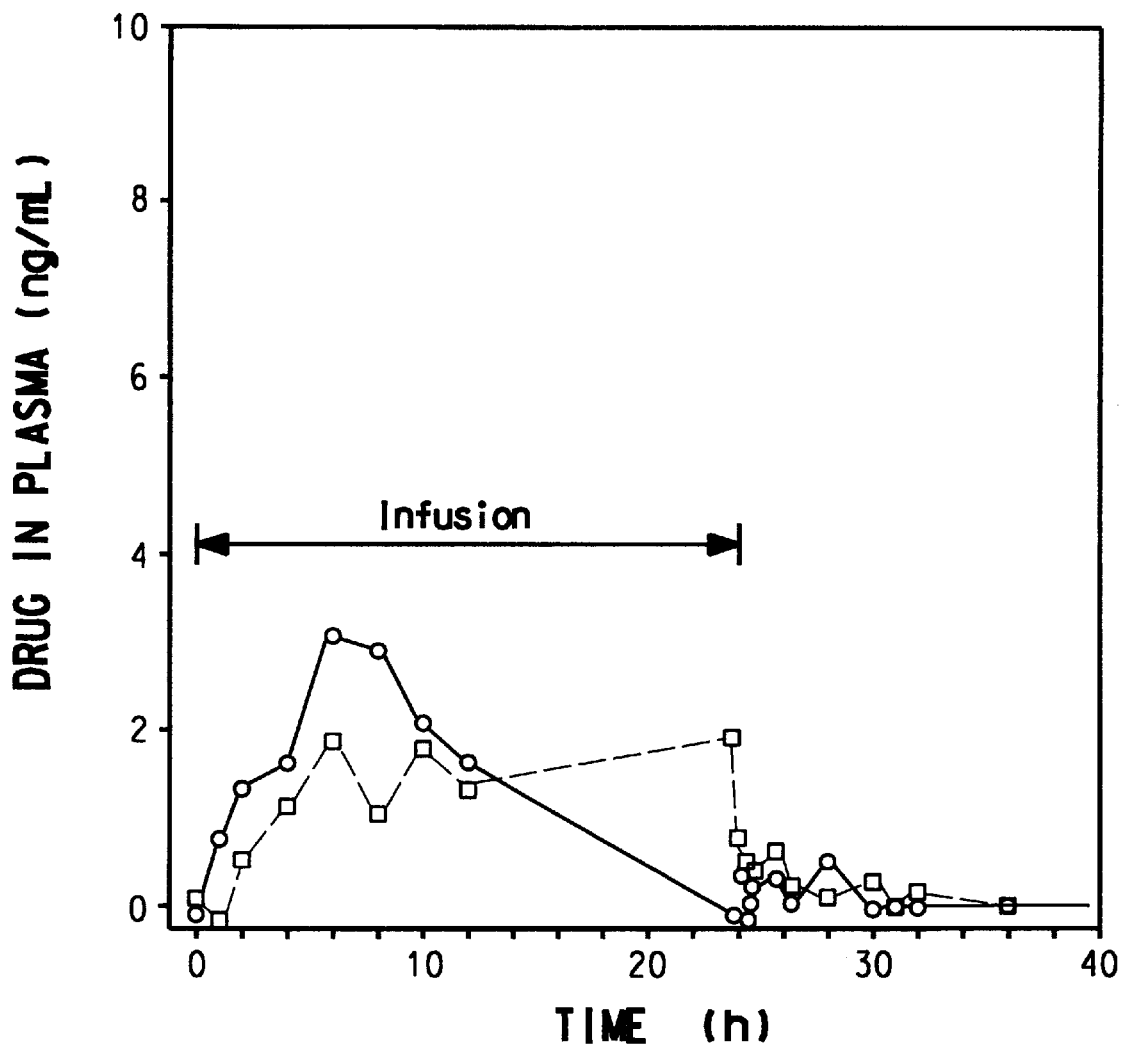
FIG. 4 shows plasma concentrations of Compound B (the acid form of Compound A) during IV infusion of Compound B at an infusion rate of 10 $\mu$g/h in unanesthetized swine.
Figure 5:
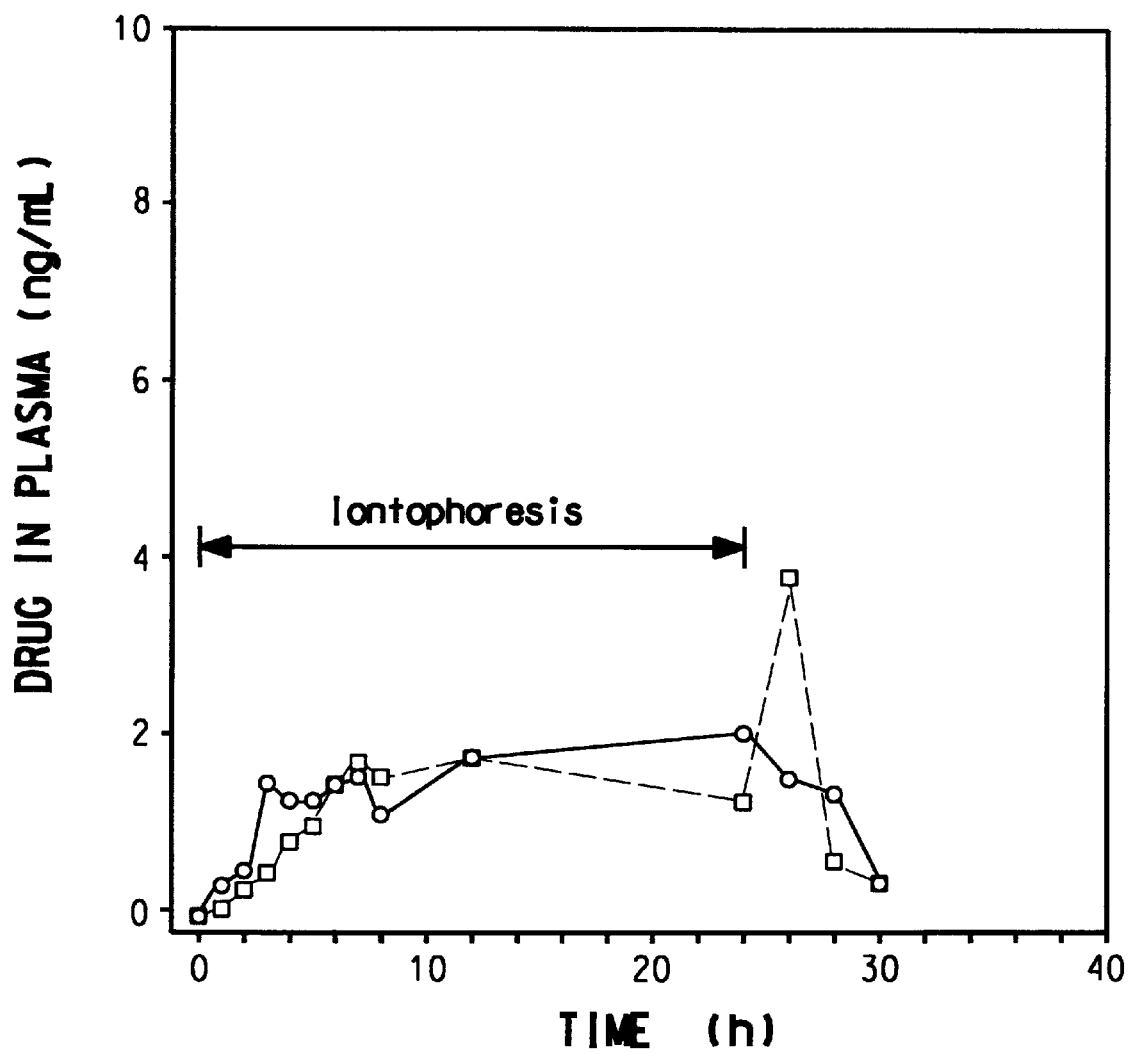
FIG. 5 shows the plasma concentration of Compound A following iontophoretic delivery in unanesthetized swine using a 2 cm$^2$ patch containing 20 mg/mL of Compound A and 154 mM NaCl at 200 $\mu$A.

FIGS. 4 and 5 compare the in vivo delivery of Compound A to pigs using constant iontophoresis (FIG. 5) and and the delivery of Compound B by constant IV infusion (FIG. 4). The results show that blood levels obtained from both delivery techniques is similar and the variability in plasma levels seen with the iontophoresis is extremely low.

What is claimed is:

1. An iontophoretic device comprising an integrin inhibitor compound of Formula I:

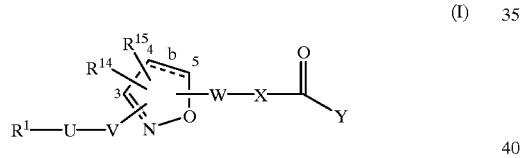

(I)

or a pharmaceutically acceptable salt form thereof wherein:
b is a carbon-carbon single or double bond;
$R^1$ is selected from $R^{2a}(R^3)N—$, $R^2(R^3)N(R^2N=)C—$, $R^{2a}(R^3)N(CH_2)_pZ—$, $R^2(R^3)N(R^2N=)C(CH_2)_pZ—$, $R^2(R^3)N(R^2N=)CN(R^2)—$, $R^2(R^3)NC(O)—$, $R^2(R^5O)N(R^2N=)C—$, $R^2(R^3)N(R^5ON=)C—$;

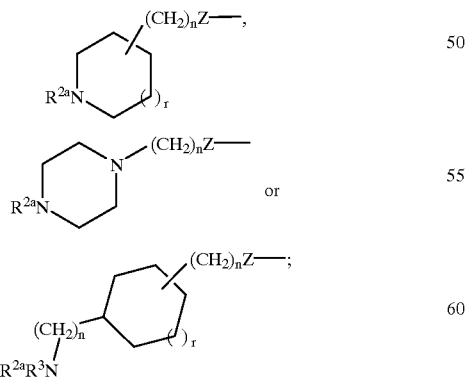

Z is selected from: a bond, O, S, S(=O), S(=O)$_2$;
$R^2$ and $R^3$ are independently selected from: H; $C_1$–$C_{10}$ alkyl; $C_3$–$C_6$ alkenyl; $C_3$–$C_{11}$ cycloalkyl; $C_4$–$C_{11}$ cycloalkylalkyl; $C_6$–$C_{10}$ aryl optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; $C_2$–$C_7$ alkylcarbonyl; $C_7$–$C_{11}$ arylcarbonyl optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; ($C_1$–$C_{10}$ alkoxy)carbonyl; $C_4$–$C_{11}$ cycloalkoxycarbonyl; $C_7$–$C_{11}$ bicycloalkoxycarbonyl; $C_7$–$C_{11}$ aryloxycarbonyl optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; ($C_1$–$C_6$ alkyl)carbonyloxy($C_1$–$C_4$ alkoxy)carbonyl; ($C_6$–$C_{10}$ aryl)carbonyloxy($C_1$–$C_4$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; ($C_4$–$C_{11}$ cycloalkylcarbonyl)oxy ($C_1$–$C_4$ alkoxy)carbonyl; heteroaryl optionally substituted with 0–2 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, $—N(CH_3)_2$, $C_1$–$C_4$ haloalkyl, methylenedioxydiyl, ethylenedioxydiyl;

provided that only one of $R^2$ and $R^3$ may be hydroxy;
$R^{2a}$ is $R^2$ or $R^2(R^3)N(R^2N=)C—$;
U is selected from:
  a single bond,
  $—(C_1–C_7 \text{ alkyl})—$,
  $—(C_2–C_7 \text{ alkenyl})—$,
  $—(C_2–C_7 \text{ alkynyl})—$;
V is selected from:
  a single bond;
  $—(C_1–C_7 \text{ alkyl})—$, substituted with 0–3 groups independently selected from $R^6$ or $R^7$;
  $—(C_2–C_7 \text{ alkenyl})—$, substituted with 0–3 groups independently selected from $R^6$ or $R^7$;
  $—(C_2–C_7 \text{ alkynyl})—$, substituted with 0–3 groups independently selected from $R^6$ or $R^7$;
  $—(phenyl)—Q—$, said phenyl substituted with 0–2 groups independently selected from $R^6$ or $R^7$;
  $—(pyridyl)—Q—$, said pyridyl substituted with 0–2 groups independently selected from $R^6$ or $R^7$; or
  $—(pyridazinyl)—Q—$, said pyridazinyl substituted with 0–2 groups independently selected from $R^6$ or $R^7$,
Q is selected from:
  a single bond,
  $—O—$, $—S(O)_m—$, $—N(R^{12})—$, $—(CH_2)_m—$, $—C(=O)—$,
  $—N(R^{5a})C(=O)—$, $—C(=O)N(R^{5a})—$, $—CH_2O—$,
  $—OCH_2—$, —$CH_2N(R^{12})$—, —$N(R^{12})CH_2$—, —$CH_2C(=O)$—, —$C(=O)CH_2$—, —$CH_2S(O)_m$—, or —$S(O)_mCH_2$—, provided that when b is a single bond, and $R^1$—U—V— is a substituent on C5 of the central 5-membered ring of Formula I, then Q is not —O—, —$S(O)_m$—, —$N(R^{12})$—, —$C(=O)N(R^{5a})$—, —$CH_2O$—, $CH_2N(R^{12})$— or —$CH_2S(O)_m$—;

W is selected from: —$(C(R^4)_2)_{n'}C(=O)N(R^{5a})$— or —$C(=O)$—$N(R^{5a})$—$(C(R^4)_2)_{n'}$—;

X is —$(C(R^4)_2)_{n'}$—$C(R^4)(R^8)$—$C(R^4)(R^{4a})$—;

Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{11}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, $(R^2)$ $(R^3)$ N— ($C_1$–$C_{10}$ alkoxy)—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

alternately, two $R^4$ groups on adjacent carbon atoms may join to form a bond thereby to form a carbon-carbon double or triple bond between such adjacent carbon atoms;

$R^{4a}$ is selected from hydroxy, $C_1$–$C_{10}$ alkoxy, nitro, $N(R^5)R^{5a}$, —$N(R^{12})R^{13}$, —$N(R^{16})R^{17}$, aryl substituted with 0–3 $R^6$, or ($C_1$–$C_{10}$ alkyl)carbonyl ;

$R^{4b}$ is selected from H, $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl , $C_6$–$C_{10}$ aryl, —$N(R^{12})R^{13}$, halo, $CF_3$, CN, ($C_1$–$C_6$ alkoxy)carbonyl , carboxy, piperidinyl, morpholinyl or pyridinyl;

$R^5$ is selected from H, $C_1$–$C_8$ alkyl, $C_3$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–6 $R^{4b}$;

$R^{5a}$ is selected from hydrogen, hydroxy, $C_1$ to $C_8$ alkyl, $C_3$–$C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, adamantylmethyl, or $C_1$–$C_{10}$ alkyl substituted with 0–2 $R^{4b}$;

alternately, $R^5$ and $R^{5a}$ when both are substituents on the same nitrogen atom (as in —$NR^5R^{5a}$) can be taken together with the nitrogen atom to which they are attached to form 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl, ($C_7$–$C_{11}$ arylalkoxy)carbonyl, $C_1$–$C_6$ alkylsulfonyl or $C_6$–$C_{10}$ arylsulfonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$;

$R^6$ is selected from H, $C_1$–$C_{10}$ alkyl, hydroxy, $C_1$–$C_{10}$ alkoxy, nitro, ($C_1$–$C_{10}$ alkyl)carbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)$ $OR^{5b}$, $NR^{5a}C(=O)NR^5R^{5a}$, $NR^{5a}SO_2NR^5R^{5a}$, $NR^{5a}SO_2R^5$, $S(O)_m R^{5a}$, $SO_2NR^5R^{5a}$, $SiMe_3$, $C_2$ to $C_6$ alkenyl, $C_3$ to $C_{11}$ cycloalkyl, $C_4$ to $C_{11}$ cycloalkylmethyl;

$C_6$ to $C_{10}$ aryl optionally substituted with 1–3 groups selected from halogen, $C_1$–$C_6$ alkoxy, $C_1$–$C_6$ alkyl, $CF_3$, $S(O)_m$Me, or —$NMe_2$;

$C_7$ to $C_{11}$ arylalkyl, said aryl being optionally substituted with 1–3 groups selected from halogen, $C_1$–$C_6$ alkoxy, $C_1$–$C_6$ alkyl, $CF_3$, $S(O)_m$Me, or —$NMe_2$;

methylenedioxy when $R^6$ is a substituent on aryl; or a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^7$;

$R^7$ is selected from H, $C_1$–$C_{10}$ alkyl, hydroxy, $C_1$–$C_{10}$ alkoxy, nitro, ($C_1$–$C_{10}$ alkyl)carbonyl, —$N(R^{12})R^{13}$, cyano, halo, $CF_3$, CHO, $CO_2R^5$, $C(=O)R^{5a}$, $CONR^5R^{5a}$, $OC(=O)R^{5a}$, $OC(=O)OR^{5b}$, $OR^{5a}$, $OC(=O)NR^5R^{5a}$, $OCH_2CO_2R^5$, $CO_2CH_2CO_2R^5$, $NO_2$, $NR^{5a}C(=O)R^{5a}$, $NR^{5a}C(=O)OR^{5b}$, $NR^{5a}C(=O)NR^5R^{5a}$, $NR^{5a}SO_2NR^5R^{5a}$, $NR^{5a}SO_2R^5$, $S(O)_m R^{5a}$, $SO_2NR^5R^{5a}$, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^8$ is selected from:

$R^6$;

$C_1$–$C_{10}$ alkyl, substituted with 0–3 $R^6$;

$C_2$–$C_{10}$ alkenyl, substituted with 0–3 $R^6$;

$C_2$–$C_{10}$ alkynyl, substituted with 0–3 $R^6$;

$C_3$–$C_8$ cycloalkyl, substituted with 0–3 $R^6$;

$C_5$–$C_6$ cycloalkenyl, substituted with 0–3 $R^6$;

aryl, substituted with 0–3 $R^6$;

5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;

$R^{12}$ and $R^{13}$ are independently H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, aryl($C_2$–$C_{10}$ alkenyl)sulfonyl, heteroarylsulfonyl, aryl, $C_2$–$C_6$ alkenyl, $C_3$–$C_{11}$ cycloalkyl, $C_4$–$C_{11}$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylsulfonyl, heteroarylalkylcarbonyl, or aryl($C_1$–$C_{10}$ alkoxy)carbonyl, wherein said aryl groups are optionally substituted with 0–3 substituents selected from the group consisting of: $C_1$–$C_4$ alkyl, $C_1$–$C_4$ alkoxy, halo, $CF_3$, and $NO_2$;

$R^{14}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, $CO_2R^5$ or —$C(=O)N(R^5)R^{5a}$;

$R^{15}$ is selected from:

H; $R^6$; —$CO_2R^5$; —$C(=O)N(R^5)R^{5a}$;
$C_1$–$C_{10}$ alkoxycarbonyl substituted with 0–2 $R^6$;
$C_1$–$C_{10}$ alkyl, substituted with 0–3 $R^6$;
$C_2$–$C_{10}$ alkenyl, substituted with 0–3 $R^6$;
$C_2$–$C_{10}$ alkoxy, substituted with 0–3 $R^6$;
aryl, substituted with 0–3 $R^6$; or
5–10 membered heterocyclic ring containing 1–3 N, O, or S heteroatoms, wherein said heterocyclic ring may be saturated, partially saturated, or fully unsaturated, said heterocyclic ring being substituted with 0–2 $R^6$;
provided that when b is a double bond, only one of $R^{14}$ or $R^{15}$ is present;
$R^{16}$ is selected from:
—C(=O)—O—$R^{18a}$,
—C(=O)$R^{18b}$,
—C(=O)N($R^{18b}$)$_2$,
—C(=O)NHSO$_2R^{18a}$,
—C(=O)NHC(=O)$R^{18b}$,
—C(=O)NHC(=O)O$R^{18a}$,
—C(=O)NHSO$_2$NHR$^{18b}$,
—C(=S)—NH—$R^{18b}$,
—NH—C(=O)—O—$R^{18a}$,
—NH—C(=O)—$R^{18b}$,
—NH—C(=O)—NH—$R^{18b}$,
—SO$_2$—O—$R^{18a}$,
—SO$_2$—$R^{18a}$,
—SO$_2$—N($R^{18b}$)$_2$,
—SO$_2$—NHC(=O) O$R^{18b}$,
—P(=S) (O$R^{18a}$)$_2$,
—P(=O) (O$R^{18a}$)$_2$,
—P(=S) ($R^{18a}$)$_2$,
—P(=O) ($R^{18a}$)$_2$, or

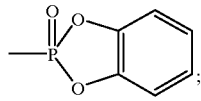

$R^{17}$ is selected from: H, $C_1$–$C_{10}$ alkyl, $C_2$–$C_6$ alkenyl, $C_3$–$C_{11}$ cycloalkyl, $C_4$–$C_{15}$ cycloalkylalkyl, aryl, aryl ($C_1$–$C_{10}$ alkyl)—;
$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)—substituted with 0–4 $R^{19}$,
a 5–10 membered heterocyclic ring system having 1–3 heteroatoms selected independently from O, S, and N, said heterocyclic ring being substituted with 0–4 $R^{19}$,
$C_1$–$C_6$ alkyl substituted with a 5–10 membered heterocyclic ring system having 1–3 heteroatoms selected independently from O, S, and N, said heterocyclic ring being substituted with 0–4 $R^{19}$;
$R^{18b}$ is selected from $R^{18a}$ or H;
$R^{19}$ is selected from H, halogen, $CF_3$, CN, $NO_2$, $NR^{12}R^{13}$, $C_1$–$C_8$ alkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl, aryl($C_1$–$C_6$ alkyl)—, $C_1$–$C_6$ alkoxy, heteroaryl, ($C_1$–$C_4$ alkyl) sulfonyl, aryl-sulfonyl, or $C_1$–$C_4$ alkoxycarbonyl;
m is 0–2;
n is 0–4;
n' is 0–4;
p' is 1–7;
p" is 1–7;
r is 0–3;
provided that n' are chosen such that the number of in-chain atoms connecting $R^1$ and Y is in the range of 8–18.

2. An iontophoretic device of claim 1 comprising a compound of Formula Ic:

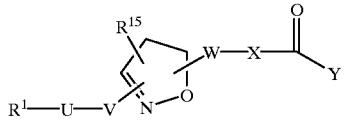

wherein:
$R^1$ is selected from $R^{2a}(R^3)N$—, $R^2(R^3)N(R^2N=)C$—, $R^{2a}(R^3)N(CH_2)_{p'}Z$—, $R^2(R^3)N(R^2N=)C(CH_2)_{p''}Z$—, $R^2(R^3)N(R^2N=)CN(R^2)$—, $R^2(R^3)NC(O)$—, $R^2(R^5O)N(R^2N=)C$—, $R^2(R^3)N(R^5ON=)C$—;

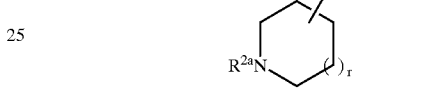

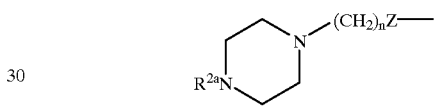

or

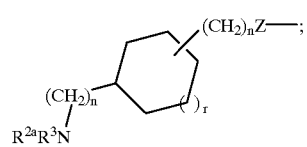

Z is selected from a bond, O, or S;
$R^2$ and $R^3$ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; ($C_1$–$C_{10}$ alkoxy)carbonyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydiyl; or heteroaryl($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, —$N(CH_3)_2$, $C_1$–$C_4$ haloalkyl, methylenedioxydiyl, ethylenedioxydlyl;
$R^{2a}$ is $R^2$ or $R^2(R^3)N(R^2N=)C$;
U is a single bond,
V is selected from: a single bond;
—($C_1$–$C_7$ alkyl)—, substituted with 0–3 groups independently selected from $R^6$ or $R^7$;
—($C_2$–$C_7$ alkenyl)—, substituted with 0–3 groups independently selected from $R^6$ or $R^7$;
—($C_2$–$C_7$ alkynyl)—, substituted with 0–3 groups independently selected from $R^6$ or $R^7$;
—(phenyl)—Q—, said phenyl substituted with 0–2 groups independently selected from $R^6$ or $R^7$;
—(pyridyl)—Q—, said pyridyl substituted with 0–2 groups independently selected from $R^6$ or $R^7$; or —(pyridazinyl)—Q—, said pyridazinyl substituted with 0–2 groups independently selected from $R^6$ or $R^7$, Q is selected from
a single bond,
—O—, —S(O)$_m$—, —N(R$^{12}$)—, —(CH$_2$)$_m$—, —C(=O)—,
—N(R$^{5a}$)C(=O)—, —C(=O)N(R$^{5a}$)—, —CH$_2$O—, —OCH$_2$—,
—CH$_2$N(R$^{12}$)—, —N(R$^{12}$)CH$_2$—, —CH$_2$C(=O)—, —C(=O)CH$_2$—,
—CH$_2$S(O)$_m$—, or —S(O)$_m$CH$_2$—, provided that when b is a single bond, and $R^1$—U—V— is a substituent on $C_5$ of the central 5-membered ring of Formula Ic, then Q is not —O—, —S(O)$_m$—, —N(R$^{12}$)—, —C(=O)N(R$^{5a}$)—, —CH$_2$O—, CH$_2$N (R$^{12}$)— or —CH$_2$S(O)$_m$—;

W is selected from: —(C(R$^4$)$_2$)—C(=O)—N(R$^{5a}$)— or —C(=O)—N(R$^{5a}$)—(C(R$^4$)$_2$)—;

X is —C(R$^4$) (R$^8$)—CHR$^{4a}$—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from hydroxy, $C_1$–$C_{10}$ alkoxy, nitro, —N(R$^5$)R$^{5a}$, —N(R$^{12}$)R$^{13}$, or —N(R$^{16}$)R$^{17}$, aryl substituted with 0–3 $R^6$, or ($C_1$–$C_{10}$ alkyl)carbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —N(R$^{12}$)R$^{13}$, halo, CF$_3$, CN, ($C_1$–$C_6$ alkoxy)carbonyl, carboxy, piperidinyl, morpholinyl or pyridyl;

$R^5$ is selected from H or $C_1$–$C_{10}$ alkyl substituted with 0–6 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl, $C_1$–$C_{10}$ alkyl substituted with 0–2 $R^{4b}$;

alternately, $R^5$ and $R^{5a}$ can be taken together to be 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl or ($C_7$–$C_{11}$ arylalkoxy)carbonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$–$C_{10}$ aryl, $C_7$–$C_{11}$ arylalkyl, or $C_1$–$C_{10}$ alkyl substituted with 0–2 $R^{4b}$ Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1, 3-dioxa-cyclopenten-2-one-yl)methyloxy, or $C_{10}$ to $C_{14}$ (5-aryl-1,3-dioxa-cyclopenten-2-one-yl) methyloxy;

$R^6$ and $R^7$ are each independently selected from H, $C_1$–$C_{10}$ alkyl, hydroxy, $C_1$–$C_{10}$ alkoxy, nitro, ($C_1$–$C_{10}$ alkyl)carbonyl, —N(R$^{12}$)R$^{13}$, cyano, or halo;

$R^{12}$ and $R^{13}$ are each independently selected from H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, heteroarylsulfonyl, heteroarylcarbonyl, heteroarylalkylcarbonyl or aryl, wherein said aryl groups being optionally substituted with 0–3 substituents selected from the group consisting of: $C_1$–$C_4$ alkyl, $C_1$–$C_4$ alkoxy, halo, CF$_3$, and NO$_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, CO$_2$R$^5$ or —C(=O)N(R$^5$) R$^{5a}$;

$R^{16}$ is selected from:
—C(=O)—OR$^{18a}$,
—C(=O)—R$^{18b}$,
—C(=O) N (R$^{18b}$)$_2$,
—SO$_2$—R$^{18a}$, or
—SO$_2$—N(R$^{18b}$)$_2$;

$R^{17}$ is selected from: H or $C_1$–$C_5$ alkyl;

$R^{18a}$ is selected from:
$C_1$–$C_8$ alkyl substituted with 0–2 $R^{19}$,
$C_2$–$C_8$ alkenyl substituted with 0–2 $R^{19}$,
$C_2$–$C_8$ alkynyl substituted with 0–2 $R^{19}$,
$C_3$–$C_8$ cycloalkyl substituted with 0–2 $R^{19}$,
aryl substituted with 0–4 $R^{19}$,
aryl($C_1$–$C_6$ alkyl)—substituted with 0–4 $R^{19}$,
a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
$C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$;

$R^{18b}$ is selected from $R^{18a}$ or H;

$R^{19}$ is selected from H, halogen, CF$_3$, CN, NO$_2$, NR$^{12}$R$^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)—, ($C_1$–$C_4$ alkyl) sulfonyl, aryl-sulfonyl, or $C_1$–$C_4$ alkoxycarbonyl;

n is 0–4;

p' is 1–7;

p" is 1–7;

r is 0–3.

3. An iontophoretic device of claim 1 comprising a compound of Formula Ib:

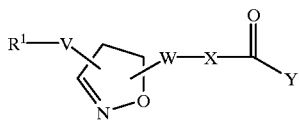

(Ib)

wherein:

R¹ is selected from: $R^{2a}(R^3)N-$, $R^2NH(R^2N=)C-$, $R^2NH(R^2N=)CNH-$, $R^{2a}(R^3)N(CH_2)_{p'}Z-$, $R^2NH(R^2N=)C(CH_2)_{p''}Z-$, $R^2(R^3)NC(O)-$, $R^2(R^5O)N(R^2N=)C-$, $R^2(R^3)N(R^5ON=)C-$;

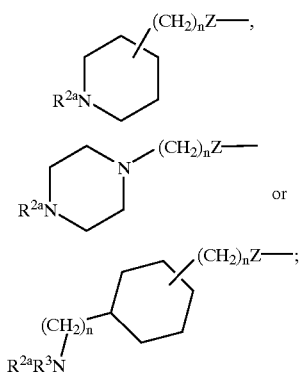

n is 0–1;
p' is 4–6;
p" is 2–4;
Z is selected from a bond or O;
V is a single bond, —(phenyl)— or —(pyridyl)—;
W is selected from: $-(C(R^4)_2)-C(=O)-N(R^{5a})-$ or $-C(=O)-N(R^{5a})-CH_2-$;
X is selected from:
$-CH_2-CH(N(R^{16})R^{17})-$ or $-CH_2-CH(NR^5R^{5a})-$;
Y is selected from:
  hydroxy;
  $C_1$ to $C_{10}$ alkoxy;
  methylcarbonyloxymethoxy-;
  ethylcarbonyloxymethoxy-;
  t-butylcarbonyloxymethoxy-;
  cyclohexylcarbonyloxymethoxy-;
  1—(methylcarbonyloxy)ethoxy-;
  1—(ethylcarbonyloxy)ethoxy-;
  1—(t-butylcarbonyloxy)ethoxy-;
  1—(cyclohexylcarbonyloxy)ethoxy-;
  i-propyloxycarbonyloxymethoxy-;
  t-butyloxycarbonyloxymethoxy-;
  1—(i-propyloxycarbonyloxy)ethoxy-;
  1—(cyclohexyloxycarbonyloxy)ethoxy-;
  1—(t-butyloxycarbonyloxy)ethoxy-;
  dimethylaminoethoxy-;
  diethylaminoethoxy-;
  (5-methyl-1,3-dioxacyclopenten-2-on-4-yl)methoxy-;
  (5-(t-butyl)-1,3-dioxacyclopenten-2-on-4-yl)methoxy-;
  (1,3-dioxa-5-phenyl-cyclopenten-2-on-4-yl)methoxy-;
  1—(2-(2-methoxypropyl)carbonyloxy)ethoxy-;
$R^{16}$ is selected from:
  $-C(=O)-O-R^{18a}$,
  $-C(=O)-R^{18b}$,
  $-S(=O)_2-R^{18a}$ or
  $-SO_2-N(R^{18b})_2$;
$R^{17}$ is selected from H or $C_1-C_5$ alkyl;
$R^{18a}$ is selected from:
  $C_1-C_8$ alkyl substituted with 0–2 $R^{19}$,
  $C_2-C_8$ alkenyl substituted with 0–2 $R^{19}$,
  $C_2-C_8$ alkynyl substituted with 0–2 $R^{19}$,
  $C_3-C_8$ cycloalkyl substituted with 0–2 $R^{19}$,
  aryl substituted with 0–4 $R^{19}$,
  aryl($C_1-C_6$ alkyl)—substituted with 0–4 $R^{19}$,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
  $C_1-C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$.

4. An iontophoretic device of claim 3 comprising a compound wherein:
$R^1$ is $R^2NH(R^2N=)C-$ or $R^2HN(R^2N=)CNH-$ and V is phenylene or pyridylene, or
$R^1$ is and V is a single bond;
n is 1 or 2;
$R^{18a}$ is selected from:
  $C_1-C_4$ alkyl substituted with 0–2 $R^{19}$,
  $C_2-C_4$ alkenyl substituted with 0–2 $R^{19}$,
  $C_2-C_4$ alkynyl substituted with 0–2 $R^{19}$,
  $C_3-C_7$ cycloalkyl substituted with 0–2 $R^{19}$,
  aryl substituted with 0–4 $R^{19}$,
  aryl($C_1-C_4$ alkyl)—substituted with 0–4 $R^{19}$,
  a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, isoxazolinyl or morpholinyl, said heterocyclic ring being substituted with 0–4 $R^{19}$;
  $C_1-C_4$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, isoxazolinyl or morpholinyl, said heterocyclic ring being substituted with 0–4 $R^{19}$.

5. An iontophoretic device of claim 1 comprising a compound, or pharmaceutically acceptable salt forms thereof, selected from:

$N^3$-[2-{3-(4-formamidinophenyl)-isoxazolin-5(R,S)-yl}-acetyl]-N2-(phenylsulfonyl)-2,3-(S)-diaminopropanoic acid;

$N^3$-[2-{3-(4-formamidinophenyl)-isoxazolin-5(R,S)-yl}-acetyl]-N2-(4-methyl-phenyl-sulfonyl)-2,3-(S)-diaminopropanoic acid;

$N^3$-[2-{3-(4-formamidinophenyl)-isoxazolin-5(R,S)-yl}-acetyl]-N2-(butanesulfonyl)-2,3-(S)-diaminopropanoic acid;

$N^3$-[2-{3-(4-formamidinophenyl)-isoxazolin-5(R,S)-yl}-acetyl]-N2-(propanesulfonyl)-2,3-(S)-diaminopropanoic acid;

$N^3$-[2-{3-(4-formamidinophenyl)-isoxazolin-5(R,S)-yl}-acetyl]-N2-(ethanesulfonyl)-2,3-(S)-diaminopropanoic acid;

$N^3$-[2-{3-(4-formamidinophenyl)-isoxazolin-5(R,S)-yl}-acetyl]-N2-(methyloxycarbonyl)-2,3-(S)-diaminopropanoic acid;

$N^3$-[2-{3-(4-formamidinophenyl)-isoxazolin-5(R,S)-yl}-acetyl]-N2-(ethyloxycarbonyl)-2,3-(S)-diaminopropanoic acid;

$N^3$-[2-{3-(4-formamidinophenyl)-isoxazolin-5(R,S)-yl}-acetyl]-N2-(1-propyloxycarbonyl)-2,3-(S)-diaminopropanoic acid;

$N^3$-[2-{3-(4-formamidinophenyl)-isoxazolin-5(R,S)-yl}-acetyl]-N2-(2-propyloxycarbonyl)-2,3-(S)-diaminopropanoic acid;

$N^3$-[2-{3-(4-formamidinophenyl)-isoxazolin-5(R,S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(S)-diaminopropanoic acid;

$N^3$-[2-{3-(4-formamidinophenyl)-isoxazolin-5(S)-yl}-acetyl]-N2-(n-butyloxycarbonyl)-2,3-(S)-diaminopropanoic acid;

$N^3$-[2-{3-(4-formamidinophenyl)-isoxazolin-5(R)-yl}-acetyl]-N2-(n-butyloxycarbonyl)-2,3-(R)-diaminopropanoic acid;

$N^3$-[2-{3-(4-formamidinophenyl)-isoxazolin-5(S)-yl}-acetyl]-N2-(n-butyloxycarbonyl)-2,3-(R)-diaminopropanoic acid;

$N^3$-[2-{3-(4-formamidinophenyl)-isoxazolin-5(R,S)-yl}-acetyl]-N2-(2-butyloxycarbonyl)-2,3-(S)-diaminopropanoic acid;

$N^3$-[2-{3-(4-formamidinophenyl)-isoxazolin-5(R,S)-yl}-acetyl]-N2-(1-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(2-(2-methyl)-propyloxycarbonyl)-2,3-(S)-diaminopropanoic acid;

$N^3$-[2-{3-(4-formamidinophenyl)-isoxazolin-5(R,S)-yl}-acetyl]-N2-(benzyloxycarbonyl)-2,3-(S)-diaminopropanoic acid;

$N^3$-[2-{3-(4-formamidinophenyl)-isoxazolin-5(R,S)-yl}-acetyl]-N2-(benzyloxycarbonyl)-2,3-(S)-diaminopropanoic acid;

$N^3$-[2-{3-(4-formamidinophenyl)-isoxazolin-5(S)-yl}-acetyl]-N2-(benzyloxycarbonyl)-2,3-(S)-diaminopropanoic acid;

$N^3$-[2-{3-(4-formamidinophenyl)-isoxazolin-5(R,S)-yl}-acetyl]-N2-(4-methylbenzyloxycarbonyl)-2,3-(S)-diaminopropanoic acid;

$N^3$-[2-{3-(4-formamidinophenyl)-isoxazolin-5(R,S)-yl}-acetyl]-N2-(4-methoxybenzyloxycarbonyl)-2,3-(S)-diaminopropanoic acid;

$N^3$-[2-{3-(4-formamidinophenyl)-isoxazolin-5(R,S)-yl}-acetyl]-N2-(4-chlorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-bromobenzyloxycarbonyl)-2,3-(S)-diaminopropanoic acid;

$N^3$-[2-{3-(4-formamidinophenyl)-isoxazolin-5(R,S)-yl}-acetyl]-N2-(4-fluorobenzyloxycarbonyl)-2,3-(S)-diaminopropanoic acid;

$N^3$-[2-{3-(4-formamidinophenyl)-isoxazolin-5(R,S)-yl}-acetyl]-N2-(4-phenoxybenzyloxycarbonyl)-2,3-(S)-diaminopropanoic acid;

$N^3$-[2-{3-(4-formamidinophenyl)-isoxazolin-5(R,S)-yl}-acetyl]-N2-(2-(methyloxyethyl)-oxycarbonyl)-2,3-(S)-diaminopropanoic acid;

$N^3$-[2-{3-(4-formamidinophenyl)-isoxazolin-5(R,S)-yl}-acetyl]-N2-(2-pyridinylcarbonyl)-2,3-(S)-diaminopropanoic acid;

$N^3$-[2-{3-(4-formamidinophenyl)-isoxazolin-5(R,S)-yl}-acetyl]-N2-(3-pyridinylcarbonyl)-2,3-(S)-diaminopropanoic acid;

$N^3$-[2-{3-(4-formamidinophenyl)-isoxazolin-5(R,S)-yl}-acetyl]-N2-(4-pyridinyl-carbonyl)-2,3-(S)-diaminopropanoic acid;

$N^3$-[2-{3-(4-formamidinophenyl)-isoxazolin-5(R,S)-yl}-acetyl]-N2-(2-(2-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(3-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-(4-pyridinyl)-acetyl)-2,3-(S)-diaminopropanoic acid;

$N^3$-[2-{3-(4-formamidinophenyl)-isoxazolin-5(R,S)-yl}-acetyl]-N2-(2-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(3-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(4-pyridyl-methyloxycarbonyl)-2,3-(S)-diaminopropanoic acid;

$N^3$-[2-{3-(4-formamidinophenyl)-isoxazolin-5(R,S)-yl}-acetyl]-N2-(4-butyloxyphenylsulfonyl)-2,3-(S)-diaminopropanoic acid;

$N^3$-[2-{3-(4-formamidinophenyl)-isoxazolin-5(R,S)-yl}-acetyl]-N2-(2-thienylsulfonyl)-2,3-(S)-diaminopropanoic acid;

$N^3$-[2-{3-(4-formamidinophenyl)-isoxazolin-5(R,S)-yl}-acetyl]-N2-(3-methylphenylsulfonyl)-2,3-(R,S)-diaminopropanoic acid;

$N^3$-[2-{3-(4-formamidinophenyl)-isoxazolin-5(R,S)-yl}-acetyl]-N2-(3-methylphenylsulfonyl)-2,3-(S)-diaminopropanoic acid;

$N^3$-[2-{3-(4-formamidinophenyl)-isoxazolin-5(R,S)-yl}-acetyl]-N2-(3-methylphenylsulfonyl)-2,3-(R)-diaminopropanoic acid;

N³-[2-{3-(4-formamidinophenyl)-isoxazolin-5(R)-yl}-acetyl]-N2-(3-methylphenylsulfonyl)-2,3-(S)-diaminopropanoic acid;

N³-[2-{3-(4-formamidinophenyl)-isoxazolin-5(S)-yl}-acetyl]-N2-(3-methylphenylsulfonyl)-2,3-(S)-diaminopropanoic acid;

N³-[2-{3-(4-formamidinophenyl)-isoxazolin-5(S)-yl}-acetyl]-N2-(3-methylphenylsulfonyl)-2,3-(R)-diaminopropanoic acid;

N³-[2-{3-(4-formamidinophenyl)-isoxazolin-5(R)-yl}-acetyl]-N2-(3-methylphenylsulfonyl)-2,3-(R)-diaminopropanoic acid;

N³-[2-{3-(4-formamidinophenyl)-isoxazolin-5(R,S)-yl}-acetyl]-N2-(4-iodophenylsulfonyl)-2,3-(S)-diaminopropanoic acid;

N³-[2-{3-(4-formamidinophenyl)-isoxazolin-5(R,S)-yl}-acetyl]-N2-(3-trifluoromethylphenylsulfonyl)-2,3-(S)-diaminopropanoic acid;

N³-[2-{3-(4-formamidinophenyl)-isoxazolin-5(R,S)-yl}-acetyl]-N2-(3-chlorophenylsulfonyl)-2,3-(S)-diaminopropanoic acid;

N³-[2-{3-(4-formamidinophenyl)-isoxazolin-5(R,S)-yl}-acetyl]-N2-(3–2-methoxycarbonylphenylsulfonyl)-2,3-(S)-diaminopropanoic acid;

N³-[2-{3-(4-formamidinophenyl)-isoxazolin-5(R,S)-yl}-acetyl]-N2-(2,4,6-trimethylphenylsulfonyl)-2,3-(S)-diaminopropanoic acid;

N³-[2-{3-(4-formamidinophenyl)-isoxazolin-5(R,S)-yl}-acetyl]-N2-(2-chlorophenylsulfonyl)-2,3-(S)-diaminopropanoic acid;

N³-[2-{3-(4-formamidinophenyl)-isoxazolin-5(R,S)-yl}-acetyl]-N2-(4-trifluoromethylphenylsulfonyl)-2,3-(S)-diaminopropanoic acid;

N³-[2-{3-(4-formamidinophenyl)-isoxazolin-5(R,S)-yl}-acetyl]-N2-(2-trifluoromethylphenylsulfonyl)-2,3-(S)-diaminopropanoic acid;

N³-[2-{3-(4-formamidinophenyl)-isoxazolin-5(R,S)-yl}-acetyl]-N2-(2-fluorophenylsulfonyl)-2,3-(S)-diaminopropanoic acid;

N³-[2-{3-(4-formamidinophenyl)-isoxazolin-5(R,S)-yl}-acetyl]-N2-(4-fluorophenylsulfonyl)-2,3-(S)-diaminopropanoic acid;

N³-[2-{3-(4-formamidinophenyl)-isoxazolin-5(R,S)-yl}-acetyl]-N2-(4-methoxyphenylsulfonyl)-2,3-(S)-diaminopropanoic acid;

N³-[2-{3-(4-formamidinophenyl)-isoxazolin-5(R,S)-yl}-acetyl]-N2-(2,3,5,6-tetramethylphenylsulfonyl)-2,3-(S)-diaminopropanoic acid;

N³-[2-{3-(4-formamidinophenyl)-isoxazolin-5(R,S)-yl}-acetyl]-N2-(4-cyanophenylsulfonyl)-2,3-(S)-diaminopropanoic acid;

N³-[2-{3-(4-formamidinophenyl)-isoxazolin-5(R,S)-yl}-acetyl]-N2-(4-chlorophenylsulfonyl)-2,3-(S)-diaminopropanoic acid;

N³-[2-{3-(4-formamidinophenyl)-isoxazolin-5(R,S)-yl}-acetyl]-N2-(4-propylphenylsulfonyl)-2,3-(S)-diaminopropanoic acid;

N³-[2-{3-(4-formamidinophenyl)-isoxazolin-5(R,S)-yl}-acetyl]-N2-(2-phenylethylsulfonyl)-2,3-(S)-diaminopropanoic acid;

N³-[2-{3-(4-formamidinophenyl)-isoxazolin-5(R,S)-yl}-acetyl]-N2-(4-isopropylphenylsulfonyl)-2,3-(S)-diaminopropanoic acid;

N³-[2-{3-(4-formamidinophenyl)-isoxazolin-5(R,S)-yl}-acetyl]-N2-(3-phenylpropylsulfonyl)-2,3-(S)-diaminopropanoic acid;

N³-[2-{3-(4-formamidinophenyl)-isoxazolin-5(R,S)-yl}-acetyl]-N2-(3-pyridylsulfonyl)-2,3-(S)-diaminopropanoic acid;

N³-[2-{3-(4-formamidinophenyl)-isoxazolin-5(R,S)-yl}-acetyl]-N2-(phenylaminosulfonyl)-2,3-(S)-diaminopropanoic acid;

³-[2-{3-(4-formamidinophenyl)-isoxazolin-5(R,S)-yl}-acetyl]-N2-(benzylaminosulfonyl)-2,3-(S)-diaminopropanoic acid;

³-[2-({3-(4-formamidinophenyl)-isoxazolin-5(R,S)-yl}-acetyl]-N2-(dimethylaminosulfonyl)-2,3-(S)-diaminopropanoic acid;

N³-[2-{3-(2-fluoro-4-formamidinophenyl)-isoxazolin-5(R,S)-yl}-acetyl]-N2-(3-methylphenylsulfonyl)-2,3-(S)-diaminopropanoic acid;

N³-[2-{3-(2-formamidino-5-pyridinyl)-isoxazolin-5(R,S)-yl}-acetyl]-N2-(n-butyloxycarbonyl)-2,3-(S)-diaminopropanoic acid;

N³-[2-{3-(2-formamidino-5-pyridinyl)-isoxazolin-5(R,S)-yl}-acetyl]-N2-(3-methylphenylsulfonyl)-2,3-(S)-diaminopropanoic acid;

N³-[2-{3-(3-formamidino-6-pyridinyl)-isoxazolin-5(R,S)-yl}-acetyl]-N2-(n-butyloxycarbonyl)-2,3-(S)-diaminopropanoic acid;

N³-[2-{3-(3-formamidino-6-pyridinyl)-isoxazolin-5(R,S)-yl}-acetyl]-N2-(3-methylphenylsulfonyl)-2,3-(S)-diaminopropanoic acid;

N³-[2-{3-(4-formamidinophenyl)-isoxazolin-5(R,S)-yl}-acetyl]-N2-(phenylaminocarbonyl)-2,3-(S)-diaminopropanoic acid;

N³-[2-{3-(4-formamidinophenyl)-isoxazolin-5(R,S)-yl}-acetyl]-N2-(4-fluorophenylaminocarbonyl)-2,3-(S)-diaminopropanoic acid;

N³-[2-{3-(4-formamidinophenyl)-isoxazolin-5(R,S)-yl}-acetyl]-N2-(1-naphthylaminocarbonyl)-2,3-(S)-diaminopropanoic acid;

N³-[2-{3-(4-formamidinophenyl)-isoxazolin-5(R,S)-yl}-acetyl]-N2-(benzylaminocarbonyl)-2,3-(S)-diaminopropanoic acid;

N³-[2-{3-(4-formamidinophenyl)-isoxazolin-5(R,S)-yl}-acetyl]-N2-(3-bromo-2-thienylsulfonyl)-2,3-(S)-diaminopropanoic acid;

N³-[2-{3-(4-formamidinophenyl)-isoxazolin-5(R,S)-yl}-acetyl]-N2-(3-methyl-2-benzothienylsulfonyl)-2,3-(S)-diaminopropanoic acid;

N³-[2-{3-(4-formamidinophenyl)-isoxazolin-5(R,S)-yl}-acetyl]-N2-(isobutyloxycarbonyl)-2,3-(S)-diaminopropanoic acid;

N³-[2-{3-(4-formamidinophenyl)-isoxazolin-5(R)-yl}-acetyl]-N2-(isobutyloxycarbonyl)-2,3-(S)-diaminopropanoic acid;

N³-[2-{3-(4-formamidinophenyl)-isoxazolin-5(S)-yl}-acetyl]-N2-(isobutyloxycarbonyl)-2,3-(S)-diaminopropanoic acid;

N³-[2-{3-(4-formamidinophenyl)-isoxazolin-5(R,S)-yl}-acetyl]-N2-(2-cyclopropylethoxycarbonyl)-2,3-(S)-diaminopropanoic acid;

N³-[2-{3-(4-formamidinophenyl)-isoxazolin-5(R)-yl}-acetyl]-N2-(2-cyclopropylethoxycarbonyl)-2,3-(S)-diaminopropanoic acid;

$N^3$-[2-{3-(4-formamidinophenyl)-isoxazolin-5(S)-yl}-acetyl]-N2-(2-cyclopropylethoxycarbonyl)-2,3-(S)-diaminopropanoic acid;

$N^3$-[2-{3-(4-guanidinophenyl)-isoxazolin-5(R,S)-yl}-acetyl]-N2-(n-butyloxycarbonyl)-2,3-(S)-diaminopropanoic acid;

$N^3$-[2-{3-(4-guanidinophenyl)-isoxazolin-5(R)-yl}-acetyl]-N2-(n-butyloxycarbonyl)-2,3-(S)-diaminopropanoic acid;

$N^3$-[2-{3-(4-guanidinophenyl)-isoxazolin-5(R)-yl}-acetyl]-N2-(3-methylphenylsulfonyl)-2,3-(S)-diaminopropanoic acid;

$N^3$-[2-{5-(4-formamidinophenyl)-isoxazolin-3(R,S)-yl}-acetyl]-N2-(n-butyloxycarbonyl)-2,3-(S)-diaminopropanoic acid;

or a propionate ester prodrug form of said compound, wherein the hydrogen of the hydroxy group of the diaminopropanoic acid moiety is substituted with a group selected from:
methyl;
ethyl;
isopropyl;
methylcarbonyloxymemethyl-;
methylcarbonyloxymemethyl-;
t-butylcarbonyloxymemethyl-;
cyclohexylcarbonyloxymemethyl-;
1-(methylcarbonyloxy)emethyl-;
1-(ethylcarbonyloxy)emethyl-;
1-(t-butylcarbonyloxy)emethyl-;
1-(cyclohexylcarbonyloxy)emethyl-;
i-propyloxycarbonyloxymemethyl-;
cyclohexylcarbonyloxymemethyl-;
t-butyloxycarbonyloxymemethyl-;
1-(i-propyloxycarbonyloxy)emethyl-;
1-(cyclohexyloxycarbonyloxy)emethyl-;
1-(t-butyloxycarbonyloxy)emethyl-;
dimethylaminoemethyl-;
diethylaminoemethyl-;
(5-methyl-1,3-dioxacyclopenten-2-on-4-yl)memethyl-;
(5-(t-butyl)-1,3-dioxacyclopenten-2-on-4-yl)memethyl-;
(1,3-dioxa-5-phenyl-cyclopenten-2-on-4-yl)memethyl-;
1-(2-(2-methoxypropyl)carbonyloxy)ethyl-.

6. An iontophoretic device of claim 1 comprising compound, or enantiomeric or diasteriomeric forms thereof, or mixtures of enantiomeric or diasteriomeric forms thereof, or a pharmaceutically acceptable salt form thereof, selected from:

$N^3$-[2-{3-(4-formamidinophenyl)-isoxazolin-5-yl}-acetyl]-$N^2$-(phenylsulfonyl)-2,3-diaminopropanoic acid;

$N^3$-[2-{3-(4-formamidinophenyl)-isoxazolin-5-yl}-acetyl]-$N^2$-(4-methyl-phenyl-sulfonyl)-2,3-diaminopropanoic acid;

$N^3$-[2-{3-(4-formamidinophenyl)-isoxazolin-5-yl}-acetyl]-$N^2$-(butanesulfonyl)-2,3-diaminopropanoic acid;

$N^3$-[2-{3-(4-formamidinophenyl)-isoxazolin-5-yl}-acetyl]-$N^2$-(propanesulfonyl)-2,3-diaminopropanoic acid;

$N^3$-[2-{3-(4-formamidinophenyl)-isoxazolin-5-yl}-acetyl]-$N^2$-(ethanesulfonyl)-2,3-diaminopropanoic acid;

$N^3$-[2-{3-(4-formamidinophenyl)-isoxazolin-5-yl}-acetyl]-$N^2$-(methyloxycarbonyl)-2,3-diaminopropanoic acid;

$N^3$-[2-{3-(4-formamidinophenyl)-isoxazolin-5-yl}-acetyl]-$N^2$-(ethyloxycarbonyl)-2,3-diaminopropanoic acid;

$N^3$-[2-{3-(4-formamidinophenyl)-isoxazolin-5-yl}-acetyl]-$N^2$-(1-propyloxycarbonyl)-2,3-diaminopropanoic acid;

$N^3$-[2-{3-(4-formamidinophenyl)-isoxazolin-5-yl}-acetyl]-$N^2$-(2-propyloxycarbonyl)-2,3-diaminopropanoic acid;

$N^3$-[2-{3-(4-formamidinophenyl)-isoxazolin-5-yl}-acetyl]-$N^2$-(n-butyloxycarbonyl)-2,3-diaminopropanoic acid;

$N^3$-[2-{3-(4-formamidinophenyl)-isoxazolin-5-yl}-acetyl]-$N^2$-(1-(2-methyl)-propyloxycarbonyl)-2,3-diaminopropanoic acid;

$N^3$-[2-{3-(4-formamidinophenyl)-isoxazolin-5-yl}-acetyl]-$N^2$-(2-(2-methyl)-propyloxycarbonyl)-2,3-diaminopropanoic acid;

$N^3$-[2-{3-(4-formamidinophenyl)-isoxazolin-5-yl}-acetyl]-$N^2$-(benzyloxycarbonyl)-2,3-diaminopropanoic acid;

$N^3$-[2-{3-(4-formamidinophenyl)-isoxazolin-5-yl}-acetyl]-$N^2$-(4-methylbenzyloxycarbonyl)-2,3-diaminopropanoic acid;

$N^3$-[2-{3-(4-formamidinophenyl)-isoxazolin-5-yl}-acetyl]-$N^2$-(4-methoxybenzyloxycarbonyl)-2,3-diaminopropanoic acid;

$N^3$-[2-{3-(4-formamidinophenyl)-isoxazolin-5-yl}-acetyl]-$N^2$-(4-chlorobenzyloxycarbonyl)-2,3-diaminopropanoic acid;

$N^3$-[2-{3-(4-formamidinophenyl)-isoxazolin-5-yl}-acetyl]-$N^2$-(4-bromobenzyloxycarbonyl)-2,3-diaminopropanoic acid;

$N^3$-[2-{3-(4-formamidinophenyl)-isoxazolin-5-yl}-acetyl]-$N^2$-(4-fluorobenzyloxycarbonyl)-2,3-diaminopropanoic acid;

$N^3$-[2-{3-(4-formamidinophenyl)-isoxazolin-5-yl}-acetyl]-$N^2$-(4-phenoxybenzyloxycarbonyl)-2,3-diaminopropanoic acid;

$N^3$-[2-{3-(4-formamidinophenyl)-isoxazolin-5-yl}-acetyl]-$N^2$-(2-(methyloxyethyl)-oxycarbonyl)-2,3-diaminopropanoic acid;

$N^3$-[2-{3-(4-formamidinophenyl)-isoxazolin-5-yl}-acetyl]-$N^2$-(2-pyridinylcarbonyl)-2,3-diaminopropanoic acid;

$N^3$-[2-{3-(4-formamidinophenyl)-isoxazolin-5-yl}-acetyl]-$N^2$-(3-pyridinylcarbonyl)-2,3-diaminopropanoic acid;

$N^3$-[2-{3-(4-formamidinophenyl)-isoxazolin-5-yl}-acetyl]-$N^2$-(4-pyridinyl-carbonyl)-2,3-diaminopropanoic acid;

$N^3$-[2-{3-(4-formamidinophenyl)-isoxazolin-5-yl}-acetyl]-$N^2$-(2-(2-pyridinyl)-acetyl)-2,3-diaminopropanoic acid;

$N^3$-[2-{3-(4-formamidinophenyl)-isoxazolin-5-yl}-acetyl]-$N^2$-(2-(3-pyridinyl)-acetyl)-2,3-diaminopropanoic acid;

$N^3$-[2-{3-(4-formamidinophenyl)-isoxazolin-5-yl}-acetyl]-$N^2$-(2-(4-pyridinyl)-acetyl)-2,3-diaminopropanoic acid;

$N^3$-[2-{3-(4-formamidinophenyl)-isoxazolin-5-yl}-acetyl]-$N^2$-(2-pyridyl-methyloxycarbonyl)-2,3-diaminopropanoic acid;

$N^3$-[2-{3-(4-formamidinophenyl)-isoxazolin-5-yl}-acetyl]-$N^2$-(3-pyridyl-methyloxycarbonyl)-2,3-diaminopropanoic acid;

$N^3$-[2-{3-(4-formamidinophenyl)-isoxazolin-5-yl}-acetyl]-$N^2$-(4-pyridyl-methyloxycarbonyl)-2,3-diaminopropanoic acid;

$N^3$-[2-{3-(4-formamidinophenyl)-isoxazolin-5-yl}-acetyl]-$N^2$-(4-butyloxyphenylsulfonyl)-2,3-diaminopropanoic acid;

$N^3$-[2-{3-(4-formamidinophenyl)-isoxazolin-5-yl}-acetyl]-$N^2$-(2-thienylsulfonyl)-2,3-diaminopropanoic acid;

$N^3$-[2-{3-(4-formamidinophenyl)-isoxazolin-5-yl}-acetyl]-$N^2$-(3-methylphenylsulfonyl)-2,3-diaminopropanoic acid;

$N^3$-[2-{3-(4-formamidinophenyl)-isoxazolin-5-yl}-acetyl]-$N^2$-(4-iodophenylsulfonyl)-2,3-diaminopropanoic acid;

$N^3$-[2-{3-(4-formamidinophenyl)-isoxazolin-5-yl}-acetyl]-$N^2$-(3-trifluoromethylphenylsulfonyl)-2,3-diaminopropanoic acid;

$N^3$-[2-{3-(4-formamidinophenyl)-isoxazolin-5-yl}-acetyl]-$N^2$-(3-chlorophenylsulfonyl)-2,3-diaminopropanoic acid;

$N^3$-[2-{3-(4-formamidinophenyl)-isoxazolin-5-yl}-acetyl]-$N^2$-(2-methoxycarbonylphenylsulfonyl)-2,3-diaminopropanoic acid;

$N^3$-[2-{3-(4-formamidinophenyl)-isoxazolin-5-yl}-acetyl]-$N^2$-(2,4,6-trimethylphenylsulfonyl)-2,3-diaminopropanoic acid;

$N^3$-[2-{3-(4-formamidinophenyl)-isoxazolin-5-yl}-acetyl]-$N^2$-(2-chlorophenylsulfonyl)-2,3-diaminopropanoic acid;

$N^3$-[2-{3-(4-formamidinophenyl)-isoxazolin-5-yl}-acetyl]-$N^2$-(4-trifluoromethylphenylsulfonyl)-2,3-diaminopropanoic acid;

$N^3$-[2-{3-(4-formamidinophenyl)-isoxazolin-5-yl}-acetyl]-$N^2$-(2-trifluoromethylphenylsulfonyl)-2,3-diaminopropanoic acid;

$N^3$-[2-{3-(4-formamidinophenyl)-isoxazolin-5-yl}-acetyl]-$N^2$-(2-fluorophenylsulfonyl)-2,3-diaminopropanoic acid;

$N^3$-[2-{3-(4-formamidinophenyl)-isoxazolin-5-yl}-acetyl]-$N^2$-(4-fluorophenylsulfonyl)-2,3-diaminopropanoic acid;

$N^3$-[2-{3-(4-formamidinophenyl)-isoxazolin-5-yl}-acetyl]-$N^2$-(4-methoxyphenylsulfonyl)-2,3-diaminopropanoic acid;

$N^3$-[2-{3-(4-formamidinophenyl)-isoxazolin-5-yl}-acetyl]-$N^2$-(2,3,5,6-tetramethylphenylsulfonyl)-2,3-diaminopropanoic acid;

$N^3$-[2-{3-(4-formamidinophenyl)-isoxazolin-5-yl}-acetyl]-$N^2$-(4-cyanophenylsulfonyl)-2,3-diaminopropanoic acid;

$N^3$-[2-{3-(4-formamidinophenyl)-isoxazolin-5-yl}-acetyl]-$N^2$-(4-chlorophenylsulfonyl)-2,3-diaminopropanoic acid;

$N^3$-[2-{3-(4-formamidinophenyl)-isoxazolin-5-yl}-acetyl]-$N^2$-(4-propylphenylsulfonyl)-2,3-diaminopropanoic acid;

$N^3$-[2-{3-(4-formamidinophenyl)-isoxazolin-5-yl}-acetyl]-$N^2$-(2-phenylethylsulfonyl)-2,3-diaminopropanoic acid;

$N^3$-[2-{3-(4-formamidinophenyl)-isoxazolin-5-yl}-acetyl]-$N^2$-(4-isopropylphenylsulfonyl)-2,3-diaminopropanoic acid;

$N^3$-[2-{3-(4-formamidinophenyl)-isoxazolin-5-yl}-acetyl]-$N^2$-(3-phenylpropylsulfonyl)-2,3-diaminopropanoic acid;

$N^3$-[2-{3-(4-formamidinophenyl)-isoxazolin-5-yl}-acetyl]-$N^2$-(3-pyridylsulfonyl)-2,3-diaminopropanoic acid;

$N^3$-[2-{3-(4-formamidinophenyl)-isoxazolin-5-yl}-acetyl]-$N^2$-(phenylaminosulfonyl)-2,3-diaminopropanoic acid;

$N^3$-[2-{3-(4-formamidinophenyl)-isoxazolin-5-yl}-acetyl]-$N^2$-(benzylaminosulfonyl)-2,3-diaminopropanoic acid;

$N^3$-[2-{3-(4-formamidinophenyl)-isoxazolin-5-yl}-acetyl]-$N^2$-(dimethylaminosulfonyl)-2,3-diaminopropanoic acid;

$N^3$-[2-{3-(2-fluoro-4-formamidinophenyl)-isoxazolin-5-yl}-acetyl]-$N^2$-(3-methylphenylsulfonyl)-2,3-diaminopropanoic acid;

$N^3$-[2-{3-(2-formamidino-5-pyridinyl)-isoxazolin-5-yl}-acetyl]-$N^2$-(n-butyloxycarbonyl)-2,3-diaminopropanoic acid;

$N^3$-[2-{3-(2-formamidino-5-pyridinyl)-isoxazolin-5-yl}-acetyl]-$N^2$-(3-methylphenylsulfonyl)-2,3-diaminopropanoic acid;

$N^3$-[2-{3-(3-formamidino-6-pyridinyl)-isoxazolin-5-yl}-acetyl]-$N^2$-(n-butyloxycarbonyl)-2,3-diaminopropanoic acid, $N^3$-[2-{3-(3-formamidino-6-pyridinyl)-isoxazolin-5-yl}-acetyl]-$N^2$-(3-methylphenylsulfonyl)-2,3-diaminopropanoic acid, $N^3$-[2-{3-(4-formamidinophenyl)-isoxazolin-5-yl}-acetyl]-$N^2$-(phenylaminocarbonyl)-2,3-diaminopropanoic acid;

$N^3$-[2-{3-(4-formamidinophenyl)-isoxazolin-5-yl}-acetyl]-$N^2$-(4-fluorophenylaminocarbonyl)-2,3-diaminopropanoic acid;

$N^3$-[2-{3-(4-formamidinophenyl)-isoxazolin-5-yl}-acetyl]-$N^2$-(1-naphthylaminocarbonyl)-2,3-diaminopropanoic acid;

$N^3$-[2-{3-(4-formamidinophenyl)-isoxazolin-5-yl}-acetyl]-$N^2$-(benzylaminocarbonyl)-2,3-diaminopropanoic acid;

$N^3$-[2-{3-(4-formamidinophenyl)-isoxazolin-5-yl}-acetyl]-$N^2$-(3-bromo-2-thienylsulfonyl)-2,3-diaminopropanoic acid;

$N^3$-[2-{3-(4-formamidinophenyl)-isoxazolin-5-yl}-acetyl]-$N^2$-(3-methyl-2-benzothienylsulfonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(isobutyloxycarbonyl)-2,3-diaminopropanoic acid, $N^3$-[2-{3-(4-formamidinophenyl)-isoxazolin-5-yl}-acetyl]-$N^2$-(2-cyclopropylethoxycarbonyl)-2,3-diaminopropanoic acid, N³-[2-{3-(4-guanidinophenyl)-isoxazolin-5-yl}-acetyl]-N²-(n-butyloxycarbonyl)-2,3-diaminopropanoic acid;

N³-[2-{3-(4-guanidinophenyl)-isoxazolin-5-yl}-acetyl]-N²-(3-methylphenylsulfonyl)-2,3-diaminopropanoic acid;

N³-[2-{5-(4-formamidinophenyl)-isoxazolin-3-yl}-acetyl]-N²-(n-butyloxycarbonyl)-2,3-diaminopropanoic acid;

N³-[2-{3-(4-formamidinophenyl)-isoxazolin-5-yl}-acetyl]-N²-(2-bromo-phenylsulfonyl)-2,3-diaminopropionic acid;

N³-[2-{3-(4-formamidinophenyl)-isoxazolin-5-yl}-acetyl]-N²-(2-methyl-phenylsulfonyl)-2,3-diaminopropionic acid;

N³-[2-{3-(3-formamidino-6-pyridinyl)-isoxazolin-5-yl}-acetyl]-N²-(3-methylphenylsulfonyl)-2,3-diaminopropionic acid;

N³-[2-{3-(2-formamidino-5-pyridinyl)-isoxazolin-5-yl}-acetyl]-N²-(3-methylphenylsulfonyl)-2,3-diaminopropionic acid;

N³-[2-{3-(2-fluoro-4-formamidinophenyl)-isoxazolin-5-yl}-acetyl]-N²-(3-methylphenylsulfonyl)-2,3-diaminopropionic acid;

N³-[2-{3-(4-formamidinophenyl)-isoxazolin-5-yl}-acetyl]-N²-(3-bromo-phenylsulfonyl)-2,3-diaminopropionic acid;

N³-[2-{3-(4-formamidinophenyl)-isoxazolin-5-yl}-acetyl]-N²-(4-bromo-phenylsulfonyl)-2,3-diaminopropionic acid;

or a propionate ester prodrug form of said compound, wherein the hydrogen of the hydroxy group of the propanoic acid moiety is substituted with a group selected from:
methyl;
ethyl;
isopropyl;
methylcarbonyloxymethyl-;
ethylcarbonyloxymethyl-;
t-butylcarbonyloxymethyl-;
cyclohexylcarbonyloxymethyl-;
1-(methylcarbonyloxy)ethyl-;
1-(ethylcarbonyloxy)ethyl-;
1-(t-butylcarbonyloxy)ethyl-;
1-(cyclohexylcarbonyloxy)ethyl-;
i-propyloxycarbonyloxymethyl-;
cyclohexyloxycarbonyloxymethyl-;
t-butyloxycarbonyloxymethyl-;
1-(i-propyloxycarbonyloxy)ethyl-;
1-(cyclohexyloxycarbonyloxy)ethyl-;
1-(t-butyloxycarbonyloxy)ethyl-;
dimethylaminoethyl-;
diethylaminoethyl-;
(5-methyl-1,3-dioxacyclopenten-2-on-4-yl)methyl-;
(5-(t-butyl)-1,3-dioxacyclopenten-2-on-4-yl)methyl-;
(1,3-dioxa-5-phenyl-cyclopenten-2-on-4-yl)methyl-;
1-(2-(2-methoxypropyl)carbonyloxy)ethyl-;

said enantiomeric and diasteriomeric forms being selected from:
(R,S), (R,S);
(R), (R,S);
(S), (R,S);
(R), (R);
(S), (R);
(R), (S);
(S), (S).

7. An iontophoretic device of claim 6 wherein the hydrogen of the hydroxy group of the diaminopropanoic acid moiety is substituted with a group selected from:
methyl;
ethyl;
isopropyl.

8. An iontophoretic device of claim 6 wherein the pharmaceutically acceptable salt form is selected from: acetate, methanesulfonate, hydrochloride, benzenesulfonate, or para-toluenesulfonate.

9. An iontophoretic device of claim 6 comprising a compound, and pharmaceutically acceptable salt forms and propionate ester prodrug forms thereof, which is:
N³-[2-{3-(4-formamidinophenyl)-isoxazolin-5(R)-yl}-acetyl]-N²-(n-butyloxycarbonyl)-2,3-(S)-diaminopropanoic acid.

10. An iontophoretic device of claim 6 comprising a compound which is:
methyl-N³-[2-{3-(4-formamidinophenyl)-isoxazolin-5(R)-yl}-acetyl]-N²-(n-butyloxycarbonyl)-2,3-(S)-diaminopropionate methanesulfonate salt.

11. An iontophoretic device of claim 1 wherein the iontophoretic device comprises:
(a) a current distributing member;
(b) an agent reservoir containing the integrin inhibitor compound, in electrical communication with the current distributing member and adapted to be placed in ionic communication with the epithelial surface;
(c) an electrolyte reservoir containing an electrolyte, in electrical communication with an indifferent electrode and in ionic communication with an epithelial surface;
(d) an electrical power source in current delivering connection with the current distributing member and the electrolyte reservoir.

* * * * *

UNITED STATES PATENT AND TRADEMARK OFFICE
CERTIFICATE OF CORRECTION

PATENT NO. : 6,185,453 B1
DATED : February 6, 2001
INVENTOR(S) : Munir A. Hussain, Arnold J. Repta It is certified that error appears in the above-identified patent and that said Letters Patent is hereby corrected as shown below:

Column 7,
Line 39, delete the "Tub/ITIa" and insert -- IIb/IIIa --;

Column 9,
Line 17, delete the "—S($^\circ$)$_m$$^-$" and insert -- —S(O)$_m$$^-$ --;

Column 10,
Line 3, delete the "$C_6$ $C_{10}$" and insert -- $C_6$ to $C_{10}$ --;
Line 52, delete the "$C_3$ to $C_1$" and insert -- $C_3$ to $C_{11}$ --;

Column 11,
Line 6, delete the "$C_7$—$C_1$1" and insert -- $C_7$-$C_{11}$ --;

Column 13
Line 36, delete the "($R^{5a}$)–(C($R^4$)2–" and insert -- ($R^{5a}$)–(C($R^4$)2)– --;

Column 14,
Line 8, delete the "$C_2$ $C_{10}$" and insert – $C_2$ to $C_{10}$ --;
Line 9, delete the "$C_5$ $C_{10}$" and insert – $C_5$ to $C_{10}$ --;
Line 15, delete the "$C_5$ $C_{10}$" and insert – $C_5$ to $C_{10}$ --;
Line 24, delete the "(CI-Clo alkyl)" and insert -- ($C_1$-$C_{10}$ alkyl) --;

Column 21,
Line 35, delete the "methylcarbonyloxymemethyl-" and insert -- methylcarbonyloxymethyl- --;
Line 36, delete the "ethylcarbonyloxymemethyl-" and insert -- ethylcarbonyloxymethyl- --;
Line 37, delete the "t-butylcarbonyloxymemethyl-" and insert -- t-butylcarbonyloxymethyl- --;
Line 38, delete the "cyclohexylcarbonyloxymemethyl-" and insert -- cyclohexylcarbonyloxymethyl- --;
Line 39, delete the "1-(methylcarbonyloxy)emethyl-" and insert -- 1-(methylcarbonyloxy)ethyl- --;
Line 40, delete the "1-(ethylcarbonyloxy)emethyl-" and insert -- 1-(ethylcarbonyloxy)ethyl- --;
Line 41, delete the "1-(t-butylcarbonyloxy)emethyl-" and insert -- 1-(t-butylcarbonyloxy)ethyl- --;

UNITED STATES PATENT AND TRADEMARK OFFICE
CERTIFICATE OF CORRECTION

PATENT NO. : 6,185,453 B1
DATED : February 6, 2001
INVENTOR(S) : Munir A. Hussain, Arnold J. Repta It is certified that error appears in the above-identified patent and that said Letters Patent is hereby corrected as shown below:

Column 21,
Line 42, delete the "1-(cyclohexylcarbonyloxy)emethyl-" and insert
-- 1-(cyclohexylcarbonyloxy)ethyl- --;
Line 43, delete the "i-proploxycarbonyloxymemethyl-" and insert -- i-propyloxycarbonyloxymethyl- --;
Line 44, delete the "cyclohexylcarbonyloxymemethyl-" and insert
-- cyclohexylcarbonyloxymethyl- --;
Line 45, delete the "t-butyloxycarbonyloxymemethyl-" and insert
-- t-butyloxycarbonyloxymethyl- --;
Line 46, delete the "1-(i-propyloxycarbonyloxy)emethyl-" and insert -- 1-(i-propyloxycarbonyloxy)ethyl- --;
Line 47, delete the "1-(cyclohexyloxycarbonyloxy)emethyl-" and insert
-- 1-(cyclohexyloxycarbonyloxy)ethyl- --;
Line 48, delete the "1-(t-butyloxycarbonyloxy)emethyl-" and insert -- 1-(t-butyloxycarbonyloxy)ethyl- --;
Line 49, delete the "dimethylaminoemethyl-" and insert -- dimethylaminoethyl- --;
Line 50, delete the "diethylaminoemethyl-" and insert -- diethylaminoethyl- --;
Line 51, delete the "memethyl-" and insert -- methyl- --;
Line 53, delete the "memethyl-" and insert -- methyl- --;
Line 55, delete the "memethyl-" and insert -- methyl- --;

Column 25,
Line 51, delete the "methylcarbonyloxymemethyl-" and insert --
methylcarbonyloxymethyl- --;
Line 52, delete the "ethylcarbonyloxymemethyl-" and insert --
ethylcarbonyloxymethyl- --;
Line 53, delete the "t-butylcarbonyloxymemethyl-" and insert --
t-butylcarbonyloxymethyl- --;
Line 54, delete the "cyclohexylcarbonyloxymemethyl-" and insert
-- cyclohexylcarbonyloxymethyl- --;
Line 55, delete the "1-(methylcarbonyloxy)emethyl-" and insert --
1-(methylcarbonyloxy)ethyl- --;
Line 56, delete the "1-(ethylcarbonyloxy)emethyl-" and insert -- 1-(ethylcarbonyloxy)ethyl- --;
Line 57, delete the "1-(t-butylcarbonyloxy)emethyl-" and insert
-- 1-(t-butylcarbonyloxy)ethyl- --;
Line 58, delete the "1-(cyclohexylcarbonyloxy)emethyl-" and insert
-- 1-(cyclohexylcarbonyloxy)ethyl- --;
Line 59, delete the "i-proploxycarbonyloxymemethyl-" and insert -- i-propyloxycarbonyloxymethyl- --;

UNITED STATES PATENT AND TRADEMARK OFFICE
CERTIFICATE OF CORRECTION

PATENT NO. : 6,185,453 B1
DATED : February 6, 2001
INVENTOR(S) : Munir A. Hussain, Arnold J. Repta It is certified that error appears in the above-identified patent and that said Letters Patent is hereby corrected as shown below:

Column 25,
Line 60, delete the "cyclohexylcarbonyloxymemethyl-" and insert
-- cyclohexylcarbonyloxymethyl- --;
Line 61, delete the "t-butyloxycarbonyloxymemethyl-" and insert
-- t-butyloxycarbonyloxymethyl- --;
Line 62, delete the "1-(i-propyloxycarbonyloxy)emethyl-" and insert -- 1-(i-propyloxycarbonyloxy)ethyl- --;
Line 63, delete the "1-(cyclohexyloxycarbonyloxy)emethyl-" and insert
-- 1-(cyclohexyloxycarbonyloxy)ethyl- --;
Line 64, delete the "1-(t-butylcarbonyloxy)emethyl-" and insert -- 1-(t-butylcarbonyloxy)ethyl- --;
Line 65, delete the "dimethylaminoemethyl-" and insert -- dimethylaminoethyl- --;
Line 66, delete the "diethylaminoemethyl-" and insert -- diethylaminoethyl- --;
Line 67, delete the "memethyl-" and insert -- methyl- --;

Column 26,
Line 2, delete the "memethyl-" and insert -- methyl- --;
Line 4, delete the "memethyl-" and insert -- methyl- --;
Line 5, delete the "emethyl-" and insert -- ethyl- --;

Column 34,
Line 54, delete the $\alpha_{v\beta3}$ " and insert -- $\alpha_v\beta_3$ --;

Column 35,
Line 22, delete the "=animal" and insert -- animal --;
Line 39, delete the $\alpha_{v\beta3}$ " and insert -- $\alpha_v\beta_3$ --;
Line 62, delete the "$\beta_v\beta_3$" and insert -- $\alpha_v\beta_3$ --;

Column 37,
Line 53, delete the "125I" and insert -- $^{125}$I --;

Column 43,
Line 19, delete the "$C_5$ $C_{10}$" and insert -- $C_5$ to $C_{10}$ --;

Column 50,
Line 1, delete the "—C(=O)—RI $^{8b}$" and insert -- —C(=O)—R$^{18b}$ --;

Column 54,
Line 11, delete the "$^3$-" and insert -- N$^3$- --;
Line 14, delete the "$^3$-" and insert -- N$^3$- --;

UNITED STATES PATENT AND TRADEMARK OFFICE
CERTIFICATE OF CORRECTION

PATENT NO. : 6,185,453 B1
DATED : February 6, 2001
INVENTOR(S) : Munir A. Hussain, Arnold J. Repta It is certified that error appears in the above-identified patent and that said Letters Patent is hereby corrected as shown below:

Column 55,
Line 22, delete the ""methylcarbonyloxymemethyl-" and insert
-- methylcarbonyloxymethyl- --;
Line 23, delete the "methylcarbonyloxymemethyl-" and insert
-- ethylcarbonyloxymethyl- --;
Line 24, delete the "t-butylcarbonyloxymemethyl-" and insert
-- t-butylcarbonyloxymethyl- --;
Line 25, delete the "cyclohexylcarbonyloxymemethyl-" and insert
-- cyclohexylcarbonyloxymethyl- --;
Line 26, delete the "1-(methylcarbonyloxy)emethyl-" and insert
-- 1-(methylcarbonyloxy)ethyl- --;
Line 27, delete the "1-(ethylcarbonyloxy)emethyl-" and insert
-- 1-(ethylcarbonyloxy)ethyl- --;
Line 28, delete the "1-(t-butylcarbonyloxy)emethyl-" and insert
-- 1-(t-butylcarbonyloxy)ethyl- --;
Line 29, delete the "1-(cyclohexylcarbonyloxy)emethyl-" and insert
-- 1-(cyclohexylcarbonyloxy)ethyl- --;
Line 30, delete the "i-propyloxycarbonyloxymemethyl-" and insert
-- i-propyloxycarbonyloxymethyl- --;
Line 31, delete the "cyclohexylcarbonyloxymemethyl-" and insert
-- cyclohexylcarbonyloxymethyl- --;
Line 32, delete the "t-butyloxycarbonyloxymemethyl-" and insert
-- t-butyloxycarbonyloxymethyl- --;
Line 33, delete the "1-(i-propyloxycarbonyloxy)emethyl-" and insert -- 1-(i-proploxycarbonyloxy)ethyl- --;
Line 34, delete the "1-(cyclohexyloxycarbonyloxy)emethyl-" and insert
-- 1-(cyclohexyloxycarbonyloxy)ethyl- --;
Line 35, delete the "1-(t-butyloxycarbonyloxy)emethyl-" and insert
-- 1-(t-butyloxycarbonyloxy)ethyl- --;
Line 36, delete the "dimethylaminoemethyl-" and insert -- dimethylaminoethyl- --;
Line 37, delete the "diethylaminoemethyl-" and insert -- diethylaminoethyl- --;

UNITED STATES PATENT AND TRADEMARK OFFICE
CERTIFICATE OF CORRECTION

PATENT NO. : 6,185,453 B1
DATED : February 6, 2001
INVENTOR(S) : Munir A. Hussain, Arnold J. Repta It is certified that error appears in the above-identified patent and that said Letters Patent is hereby corrected as shown below:

<u>Column 55,</u>
Line 38, delete the "memethyl-" and insert -- methyl- --;
Line 40, delete the "memethyl-" and insert -- methyl- --;
Line 42, delete the "memethyl-" and insert -- methyl- --;

Signed and Sealed this

Thirteenth Day of November, 2001

Attest:

NICHOLAS P. GODICI
Attesting Officer    Acting Director of the United States Patent and Trademark Office